United States Patent [19]
Dunn et al.

[11] Patent Number: 5,622,948
[45] Date of Patent: Apr. 22, 1997

[54] PYRROLE PYRIDAZINE AND PYRIDAZINONE ANTI-INFLAMMATORY AGENTS

[75] Inventors: James P. Dunn, Los Altos; Chakk S. Ramesha, San Jose; Jim W. Barnett, La Honda; Denis J. Kertesz, Mountain View; Aaron B. Miller, Sunnyvale; David Morgans, Jr., Los Altos; C. Elliott Sigal, San Francisco; Eric B. Sjogren, Mountain View; David B. Smith, San Mateo, all of Calif.; Francisco X. Talamas, Cuernavaca, Mexico

[73] Assignee: Syntex (U.S.A.) Inc., Palo Alto, Calif.

[21] Appl. No.: 347,915

[22] Filed: Dec. 1, 1994

[51] Int. Cl.$^6$ ..................................................... A61K 31/50
[52] U.S. Cl. ........................ 514/236.5; 514/252; 544/114; 544/238
[58] Field of Search ...................... 544/238, 114; 514/252, 236.5

[56] References Cited

U.S. PATENT DOCUMENTS

| | | | |
|---|---|---|---|
| 3,586,681 | 6/1971 | Houlihan | 544/238 |
| 3,726,978 | 4/1973 | Houlihan | 514/247 |
| 3,752,826 | 8/1973 | Carson . | |
| 4,089,969 | 5/1978 | Muchowski et al. | 424/274 |
| 4,247,551 | 1/1981 | Bellasio et al. | 514/252 |
| 4,347,187 | 8/1982 | Muchowski et al. | 548/516 |
| 4,766,121 | 8/1988 | Ellis et al. | 544/238 |
| 4,816,454 | 3/1989 | Zoller | 544/238 |
| 4,992,441 | 2/1991 | Scott | 514/252 |
| 5,086,052 | 2/1992 | Brooks et al. | 544/238 |
| 5,332,736 | 7/1994 | Carmosin et al. | 548/418 |

FOREIGN PATENT DOCUMENTS

| | | |
|---|---|---|
| 0068460 | 1/1983 | European Pat. Off. . |
| 0488602A1 | 6/1992 | European Pat. Off. . |
| 2081455 | 12/1971 | France . |
| 2316942 | 2/1977 | France . |
| 2375234 | 7/1978 | France . |
| WO83/00863 | 3/1983 | WIPO . |
| WO94/06919 | 3/1994 | WIPO . |
| WO94/14977 | 7/1994 | WIPO . |

OTHER PUBLICATIONS

Meade, et al., Journal of Biological Chemistry, vol. 268:9 6610–6614 (Mar. 25, 1993, "Differential Inhibition of Prostaglandin Endoperoxide Synthase (Cyclooxygenase) Isozymes by Aspirin and Other Non–steroidal Anti–inflammatory Drugs".

Miller, et al.,Biochemical and Biophysical Research Communications, vol. 201:1, 356–362, (May 30, 1994), "The Heterologous Expression and Characterization of Human Prostaglandin G/H Synthase–2 (COX–2)".

Mitchell, et al., Proc. National Academy of Science, vol. 90: 11693–11697 (Dec. 1994), "Selectivity of nonsteroidal antinflammatory drugs as inhibitors of constitutive and inducible cyclooxygenase".

O'Neill, et al., Molecular Pharmacology, vol. 45: 245–254, (Nov. 3, 1993), "Overexpression of Human Prostaglandin G/H Synthase–1 and –2 by Recombinant Vaccinia Virus: Inhibition by Nonsteroidal Anti–inflammatory Drugs and Biosynthesis of 15–Hydroxyeicosatetraeonoic Acid".

Futaki, et al., Abstract No. 389, 8th International Conference on Prostaglandins and Related Compounds, Montreal, Canada (Jul. 26–31, 1992), "Pharmacological Studies of NS–389: A Newly synthesized Nonsteroidal Anti–inflammatory Drug With Selective Inhibition of Prostaglandin Synthesis In Inflamed Tissue,".

W.H. Rooks II et al., "The analgesic and anti–inflammatory profile of (±)–5–benzoyl–1,2–dihydro–3H–pyrrolo[1,2–a] pyrrole–1 carboxylic acid (RS–37619)", *Agents and Actions*, 12(5), 684–690 (1982).

Joseph M. Muchowski et al., "Synthesis and Antiinflammatory and Analgesic Activity of 5–Aroyl–1, 2–dihydro–3H–pyrrolo[1,2-a]pyrrole–1–carboxylic acids . . . ", *J. Med. Chem.*, 30(5), 820–823 (1987).

A.C. Goudie et al., "4,5,8,9–Tetrahydro–8–methyl–9–oxothieno[3'2':5,6]cyclohepta[1,2–b]pyrrole–7–acetic Acids (1). . .", *J. Heterocyclic Chem.*, 20(4),1027–1030 (1983).

Giuliano Nannini et al., "Synthesis and pharmacological activity of some 5,6–diphenyl–pyridazines", *Eur. J. Med. Chem.—Chim. Ther.*, 14(1), 53–60 (1979).

*Primary Examiner*—Donald G. Daus
*Attorney, Agent, or Firm*—Heller Ehrman White & McAuliffe

[57] ABSTRACT

Pyrrole pyridazine and pyridazinone compounds are described. These compounds are useful as anti-inflammatory agents in the treatment of inflammation and pain. The preparation of these compounds, their pharmaceutically acceptable salts, and pharmaceutical compositions containing these compounds, is also described.

115 Claims, No Drawings

PYRROLE PYRIDAZINE AND PYRIDAZINONE ANTI-INFLAMMATORY AGENTS

BACKGROUND OF THE INVENTION

1. Field of the Invention

Considerable effort has been devoted to the discovery of non-steroidal anti-inflammatory drugs ("NSAIDs") with reduced undesirable effects in the gastrointestinal ("GI") tract and the kidney, for example. Although modest improvements have been made in this area, an effective NSAID devoid of adverse GI and renal side effects has remained elusive.

2. Description of the Related Art

Carson, et al., U.S. Pat. No. 3,752,826 describes a family of aroyl-substituted pyrroles that are useful as anti-inflammatory agents.

Ellis, et al., U.S. Pat. No. 4,766,121 pertains to a family of pyridyl and pyridazinyl substituted thyronine compounds that exhibit thyromimetic activity.

Dowell, et al., EP Application No. 91310784.3 describes a class of 5-lipoxygenase inhibitors that are useful as anti-inflammatory agents.

The above-cited patents and the references described therein, are all incorporated herein by reference.

SUMMARY OF THE INVENTION

One aspect of the present invention relates to a family of compounds of Formula (Ia) having the following structure:

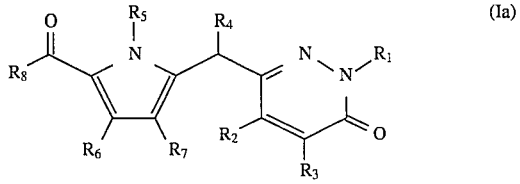

wherein:

$R_1$ is —H, lower alkyl, halo-lower alkyl, acetyl, substituted acetyl, —(CHR$_{24}$)(CH$_2$)$_n$R$_{14}$, —(CHR$_{24}$)(CH$_2$)$_n$C(O)R$_{15}$, —(CHR$_{24}$)(CH$_2$)$_n$C(O)NR$_{16}$R$_{17}$ or —CHR$_{24}$R$_{18}$; where n is an integer from 0–5, $R_{14}$ is —CN, —OH, lower alkoxy, lower acyloxy, substituted acyloxy, lower dialkylamino, lower alkylthio, lower alkylsulfinyl, lower alkylsulfonyl, lower alkene, lower alkyne or methane sulfonamido; $R_{15}$ is lower alkoxy; $R_{16}$ and $R_{17}$ are independently selected from the group consisting of —H and lower alkyl; $R_{18}$ is:

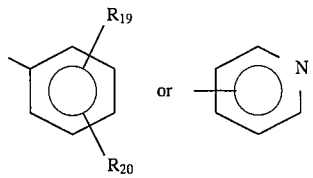

where $R_{19}$ and $R_{20}$ are independently selected from the group consisting of —CN, halo, lower alkoxy and lower alkyl; and $R_{24}$ is —H, lower alkyl or phenyl;

$R_2$ and $R_3$ are independently selected from the group consisting of —H, halo and —CH$_3$;

$R_4$ is —H, lower alkyl or —CN;

$R_5$ is —H or lower alkyl;

$R_6$ and $R_7$ are independently selected from the group consisting of —H, halo, lower alkyl, lower alkoxy and lower alkylthio; and $R_8$ is:

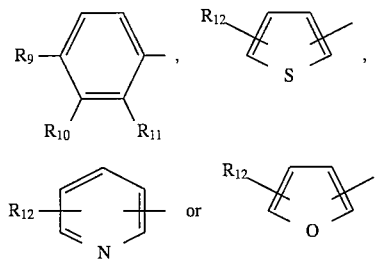

where $R_9$ is —H, halo, lower alkyl, halo-lower alkyl, amino, lower dialkylamino, lower alkyl amido, lower alkylthio, lower alkoxy, lower alkene or lower alkyne; $R_{10}$ and $R_{11}$ are independently selected from the group consisting of —H, halo and —CH$_3$; and $R_{12}$ is —H, —Cl or —CH$_3$; and the pharmaceutically acceptable salts thereof.

Yet another aspect of the present invention relates to a family of compounds of Formula (Ib) having the following structure:

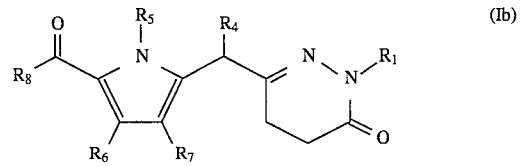

wherein $R_1$ and $R_4$ to $R_8$ are as defined above; and the pharmaceutically acceptable salts thereof.

Another aspect of the present invention relates to a family of compounds of Formula (II) having the following structure:

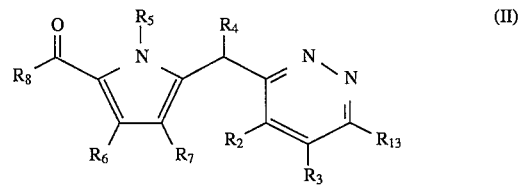

wherein: $R_2$ to $R_8$ are as defined above and $R_{13}$ is lower alkoxy, mercapto, lower alkylthio, —NR$_{21}$R$_{22}$ or —O—(CH$_2$)$_m$—NR$_{21}$R$_{22}$; where m is an integer from 1 to 6, $R_{21}$ is —H or lower alkyl and $R_{22}$ is —H or lower alkyl, and where $R_{21}$ and $R_{22}$ may be taken together with N to form a ring of three to five carbon atoms which may include one member that is —O—, —S—, or —N(R$_{23}$)— where $R_{23}$ is —H or lower alkyl; and the pharmaceutically acceptable salts thereof.

Yet another aspect of the present invention relates to a family of compounds of Formula (III) having the following structure:

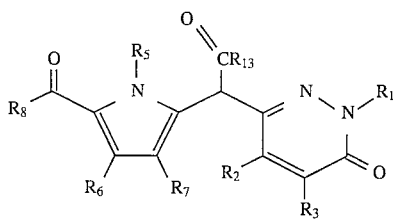

(III)

wherein: $R_1$, $R_5$ to $R_8$, and $R_{13}$ are as defined above; and the pharmaceutically acceptable salts thereof.

In another aspect, the invention relates to pharmaceutical compositions containing a therapeutically effective amount of a compound of Formula (Ia), (Ib), (II) or (III) or a pharmaceutically acceptable salt thereof, mixed with at least one pharmaceutically acceptable excipient.

In still another aspect, the invention relates to a method of use of compounds of Formula (Ia), (Ib), (II) and (III) as anti-inflammatory agents to treat inflammation and pain by administering to a mammal in need of such treatment a therapeutically effective amount of a compound of Formula (Ia), (Ib), (II) or (III) or a pharmaceutically acceptable salt thereof.

In another aspect, this invention provides compositions useful in the treatment of the above conditions comprising a therapeutically effective amount of a compound of Formula (Ia), (Ib), (II) or (III) or a pharmaceutically acceptable salt thereof, and a pharmaceutically acceptable excipient.

Another aspect of the invention pertains to a method of selecting an NSAID that will not exhibit adverse gastrointestinal ("GI") and renal side effects, comprising the step of testing the NSAID for its ability to inhibit the enzyme activity of prostaglandin G/H synthase I (cyclooxygenase I or "COX I") and prostaglandin G/H synthase II (cyclooxygenase II or "COX II"), wherein selective inhibition of COX II over COX I is indicative of a GI and renal sparing drug.

Yet another aspect of the invention relates to the treatment of the above conditions or diseases by the selective inhibition of COX II. In particular, the invention relates to a method of treating pain and inflammation without obtaining adverse GI and renal side effects, comprising the step of administering to a mammal in need of such treatment a therapeutically effective amount of a compound that selectively inhibits cyclooxygenase II over cyclooxygenase I.

DESCRIPTION OF THE SPECIFIC EMBODIMENTS

Before proceeding further with the description of the specific embodiments of the present invention, a number of terms will be defined.

The term "alkyl" refers to a monovalent radical containing only carbon and hydrogen, and which may be a fully saturated branched or straight chain radical, or a ring of carbon atoms linked together by single bonds. This term is further exemplified by radicals such as methyl (—CH$_3$), ethyl, t-butyl, pentyl, pivalyl, heptyl, cyclopropyl, cyclobutyl, cyclopentyl, cyclohexyl, cyclohexylmethyl, adamantyl, and the like.

The term "lower alkyl" refers to a monovalent saturated hydrocarbon radical of up to six carbon atoms selected from straight chain $C_1$–$C_6$ alkyl, branched chain $C_3$–$C_6$ alkyl, $C_3$–$C_6$ cycloalkyl, and $C_3$–$C_5$ cycloalkyl—$C_1$–$C_3$ alkyl. This term is further exemplified by such radicals as methyl, ethyl, n-propyl, isopropyl, n-butyl, t-butyl, i-butyl (or 2-methylpropyl), cyclopropylmethyl, i-amyl, n-amyl and hexyl.

The term "hydroxy" refers to the radical, —OH. The term "lower alkoxy" refers to the group —O—R where R is a lower alkyl.

The term "acetyl" refers to the radical —C(O)CH$_3$. The term "substituted acetyl" refers to an acetyl where 1–3 of the hydrogens have been replaced by a radical selected from the group consisting of lower alkyl, acetoxy (—O—C(O)—CH$_3$) and amino.

The term "lower acyloxy" refers to the radical, —O—C(O)—R, where R is a lower alkyl. The term "substituted acyloxy" refers to an acyloxy where 1–3 of the hydrogens have been replaced by a radical selected from the group consisting of lower alkyl, acetoxy and amino.

The term "lower alkylthio" refers to the group —S—R, where R is a lower alkyl. This term is exemplified by such radicals as methylthio, —SCH$_3$.

The term "lower alkylsulfinyl" refers to the group —S(O)—R, where R is a lower alkyl. This term is exemplified by such radicals as methylsulfinyl, —S(O)CH$_3$.

The term "lower alkylsulfonyl" refers to the group —S(O)$_2$—R, where R is a lower alkyl. This term is exemplified by such radicals as methylsulfonyl, —S(O)$_2$CH$_3$.

The term "lower alkene" refers to an unsaturated branched or straight chain alkene radical of two to six carbon atoms and containing a double bond. This term is further exemplified by such radicals as ethylene and propylene.

The term "lower alkyne" refers to an unsaturated branched or straight chain alkyne radical of two to six carbon atoms and containing a triple bond. This term is further exemplified by such radicals as acetylene, propyne and butyne.

The term "cyano" refers to the radical, —CN.

The term "halo" refers to fluoro, bromo, chloro and iodo.

The term "halo-lower alkyl" refers to a lower alkyl substituted with one to three halo groups, and is further exemplified by such radicals as —CF$_3$, —CH$_2$CF$_3$ and —CH$_2$CCl$_3$.

The term "amino" refers to the radical —NH$_2$. The term "lower dialkylamino" refers to two lower alkyl groups bound to an amino group, and is further exemplified by such radicals as dimethylamino, —N(CH$_3$)$_2$.

The term "mercapto" refers to the radical, —SH.

The term "methane sulfonamido" refers to the radical, —NHS(O)$_2$CH$_3$.

The term "pharmaceutically acceptable salt" is a salt of a compound of the invention that retains the biological effectiveness and properties of the compound of the invention and which is not biologically or otherwise undesirable. Salts may be derived from inorganic or organic acids and bases, and include pharmaceutically acceptable anions, the anions of acid addition salts, and pharmaceutically acceptable cations, the cations of base addition salts. Acid addition salts are derived from inorganic acids, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid, and the like. Base addition salts may be derived from inorganic bases such as sodium hydroxide, potassium hydroxide, lithium hydroxide, ammonium, calcium hydroxide, magnesium hydroxide, and the like. Salts derived from organic bases include those formed from primary, secondary and tertiary amines, substituted amines including naturally occurring substituted amines, and cyclic amines, including isopropylamine, trimethylamine, diethylamine, triethylamine, tripropylamine, ethanolamine, 2-dimethylaminoethanol, pyridine, cyclohexylamine, ethylene diamine, tromethamine, lysine, arginine, histidine, caffeine, procaine, hydrabamine, choline, betaine, ethylenediamine, glucosamine, N-alkylglucamines, theobromine, purines, piperazine, piperidine, N-ethylpiperidine, and the like. Preferred organic bases are isopropylamine, diethylamine, monoethanolamine, diethanolamine, triethanolamine, piperidine, tromethamine, and choline.

The naming and numbering of the compounds of the present invention is illustrated below. The pyrrole pyridazine/pyridazinone nucleus of the compounds of Formula (Ia), (Ib), (II) and (III) is numbered as follows:

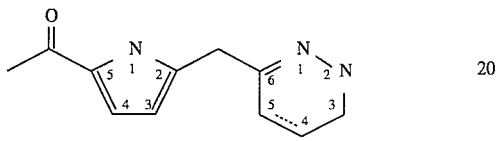

Side chains of the $R_8$ substituent are numbered as shown below:

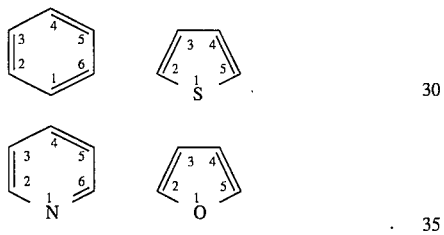

The thiophene, pyridine and furan rings can be linked to the pyrrole carbonyl group at any position on the ring. Accordingly, the thiophene ring can be 2- or 3-thienyl, the pyridine ring can be 2-, 3-, or 4-pyridyl, and the furan ring can be 2- or 3-furyl.

This invention relates to families of compounds that are non-steroidal anti-inflammatory drugs and which do not exhibit gastrointestinal ("GI") and renal side effects when administered at doses sufficient to achieve an antiinflammatory effect.

The invention relates to a family of compounds of Formula (Ia) having the following structure:

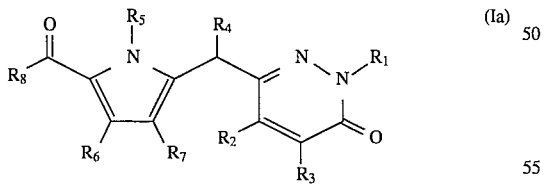

wherein:

$R_1$ is —H, lower alkyl, halo-lower alkyl, acetyl, substituted acetyl, —(CHR$_{24}$)(CH$_2$)$_n$R$_{14}$, —(CHR$_{24}$)(CH$_2$)$_n$C(O)R$_{15}$, —(CHR$_{24}$)(CH$_2$)$_n$C(O)NR$_{16}$R$_{17}$ or —CHR$_{24}$R$_{18}$; where n is an integer from 0–5, $R_{14}$ is —CN, —OH, lower alkoxy, lower acyloxy, substituted acyloxy, lower dialkylamino, lower alkylthio, lower alkylsulfinyl, lower alkylsulfonyl, lower alkene, lower alkyne or methane sulfonamido; $R_{15}$ is lower alkoxy; $R_{16}$ and $R_{17}$ are independently selected from the group consisting of —H and lower alkyl; $R_{18}$ is:

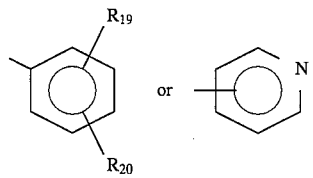

where $R_{19}$ and $R_{20}$ are independently selected from the group consisting of —CN, halo, lower alkoxy and lower alkyl; and $R_{24}$ is —H, lower alkyl or phenyl;

$R_2$ and $R_3$ are independently selected from the group consisting of —H, halo and —CH$_3$;

$R_4$ is —H, lower alkyl or —CN;

$R_5$ is —H or lower alkyl;

$R_6$ and $R_7$ are independently selected from the group consisting of —H, halo, lower alkyl, lower alkoxy and lower alkylthio; and $R_8$ is:

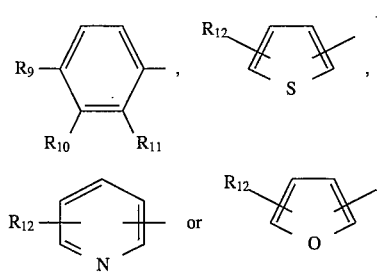

where $R_9$ is —H, halo, lower alkyl, halo-lower alkyl, amino, lower dialkylamino, lower alkyl amido, lower alkylthio, lower alkoxy, lower alkene or lower alkyne; $R_{10}$ and $R_{11}$ are independently selected from the group consisting of —H, halo and —CH$_3$; and $R_{12}$ is —H, —Cl or —CH$_3$; and the pharmaceutically acceptable salts thereof.

Representative compounds of Formula (Ia), where $R_1=R_2=R_3=R_4$=H, $R_5$=CH$_3$, $R_7$=H, and $R_8$ is a benzene ring, are as follows:

| # | $R_6$ | $R_9$ | $R_{10}$ | $R_{11}$ | Melting point, °C. (solvent of crystallization) | |
|---|---|---|---|---|---|---|
| 16 | CH$_3$ | Cl | H | H | 202–203 | (acetone:hexane) |
| 30 | CH$_3$ | CH$_3$ | H | H | 233–235 | (CH$_2$Cl$_2$:CH$_3$OH) |
| 31 | CH$_3$ | OCH$_3$ | H | H | 198–200 | (CH$_2$Cl$_2$:CH$_3$OH) |
| 32 | CH$_3$ | H | H | H | 164–166 | (CH$_2$Cl$_2$:EtOAc) |
| 33 | CH$_3$ | CHCH$_2$ | H | H | 190–192 | (hexane:acetone) |
| 34 | CH$_3$ | SCH$_3$ | H | H | 205–207 | (CH$_2$Cl$_2$:hexane) |

-continued

| # | $R_6$ | $R_9$ | $R_{10}$ | $R_{11}$ | Melting point, °C. (solvent of crystallization) | |
|---|---|---|---|---|---|---|
| 35 | $CH_3$ | Br | H | H | 224–226 | ($CH_2Cl_2$:acetone) |
| 36 | $CH_3$ | $CH_2CH_3$ | H | H | 228–229 | ($CH_3OH$:acetone) |
| 37 | H | $CH_3$ | $CH_3$ | H | 195–197 | (hexane:EtOAc) |
| 38 | H | H | $CH_3$ | H | 172–174 | (hexane:acetone) |
| 39 | H | Cl | H | H | 168–170 | (EtOAc) |
| 40 | H | H | Cl | H | 165–170 | ($CH_3OH$) |
| 41 | H | H | H | Cl | 190–192 | (EtOAc) |
| 42 | H | cyclopropyl | H | H | 182–183 | ($CH_2Cl_2$:hexane) |
| 43 | H | $SCH_3$ | H | H | 190–191 | (EtOAc) |
| 44 | H | $N(CH_3)_2$ | H | H | 178–179 | ($CH_2Cl_2$:hexane) |
| 45 | H | $CH(CH_3)_2$ | H | H | 162–163 | ($CH_2Cl_2$:hexane) |
| 46 | H | $CH_2CH_3$ | H | H | 164–166 | ($CH_2Cl_2$:hexane) |
| 47 | H | Cl | H | Cl | 179–180 | (EtOAc) |
| 48 | H | F | H | H | 200–201 | ($CH_3OH$) |
| 49 | H | H | H | $CH_3$ | 170–172 | (hexane:EtOAc) |
| 50 | H | $SCH_2CH_3$ | H | H | 164–165 | (hexane:EtOAc) |
| 51 | H | $CH_3$ | H | $CH_3$ | 166–167 | (hexane:EtOAc) |
| 52 | H | $CF_3$ | H | H | 186–188 | (hexane:EtOAc) |
| 53 | H | $OCH_3$ | H | H | 198–199 | (EtOAc) |
| 54 | H | $CHCH_2$ | H | H | 186–188 | (hexane:acetone) |
| 55 | H | $C(CH_3)_3$ | H | H | 171–173 | (EtOAc) |
| 56 | H | H | H | H | 162–163 | (hexane:acetone) |
| 57 | H | Br | H | H | 186–187 | (hexane:acetone) |
| 58 | H | $O(CH_2)_2CH_3$ | H | H | 174–176 | (hexane:acetone) |
| 59 | H | $OCH(CH_3)_2$ | H | H | 138–140 | (hexane:acetone) |
| 60 | H | $OCH_2CH_3$ | H | H | 180–182 | (hexane:acetone) |
| 65 | H | C≡CH | H | H | 185–187 | (hexane:acetone) |
| 100 | H | $CH_3$ | H | H | 227.2–227.4 | (EtOAc) |
| 106 | H | $NHCOCH_3$ | H | H | 252–254 | (acetone:$CH_3OH$) |
| 142 | $CH_3$ | F | H | H | 193–194 | ($CH_2Cl_2$:$CH_3OH$) |
| 167 | $SCH_3$ | | Cl | H | 192–193 | ($CH_2Cl_2$:hexane) | and are named:

16. 6-[1,4-dimethyl-5-(4chloro-benzoyl)-1H-pyrrol-2-ylmethyl]-2H-pyridazin-3-one;
30. 6-[1,4-dimethyl-5-(4-methyl-benzoyl)-1H-pyrrol-2-ylmethyl]-2H-pyridazin-3-one;
31. 6-[1,4-dimethyl-5-(4-methoxy-benzoyl)-1-H-pyrrol-2-ylmethyl]-2H-pyridazin-3-one;
32. 6-[5-benzoyl-1,4-dimethyl-1H-pyrrol-2-ylmethyl]-2H-pyridazin-3-one;
33. 6-[1,4-dimethyl-5-(4-vinyl-benzoyl)-1H-pyrrol-2-ylmethyl]-2H-pyridazin-3-one;
34. 6-[1,4-dimethyl-5-(4-methylthio-benzoyl)-1H-pyrrol-2-ylmethyl]-2H -pyridazin -3-one;
35. 6-[5-(4-bromo-benzoyl)-1,4-dimethyl-1H-pyrrol-2-ylmethyl]-2H-pyridazin-3-one;
36. 6-[1,4-dimethyl-5-(4-ethyl-benzoyl)-1H-pyrrol-2-ylmethyl]-2H-pyridazin-3-one;
37. 6-[5-(3,4-dimethyl-benzoyl)-1-methyl-1H-pyrrol-2-ylmethyl]-2H-pyridazin-3-one;
38. 6-[1-methyl-5-(3-methyl-benzoyl)-1H-pyrrol-2-ylmethyl]-2H-pyridazin-3-one;
39. 6-[5-(4-chloro-benzoyl)-1-methyl-1H-pyrrol-2-ylmethyl]-2H-pyridazin-3-one;
40. 6-[5-(3-chloro-benzoyl)-1-methyl-1H-pyrrol-2-ylmethyl]-2H-pyridazin-3-one;
41. 6-[5-(4-chloro-benzoyl)-1-methyl-1H-pyrrol-2-ylmethyl]-2H-pyridazin-3-one;
42. 6-[5-(4-cyclopropyl-benzoyl)-1-methyl-1H-pyrrol-2-ylmethyl]-2H-pyridazin-3-one;
43. 6-[1-methyl-5-(4-methylthio-benzoyl)-1H-pyrrol-2-yl-methyl]-2H-pyridazin-3-one;
44. 6-[5-(4-dimethylamino-benzoyl)-1-methyl-1H-pyrrol-2-ylmethyl]-2H-pyridazin-3-one;
45. 6-[5-(4-isopropyl-benzoyl)-1-methyl-1H-.pyrrol-2-ylmethyl]-2H-pyridazin-3-one;
46. 6-[5-(4-ethyl-benzoyl)-1-methyl-1H-pyrrol-2-ylmethyl]-2H-pyridazin-3-one;
47. 6-[5-(2,4-dichloro-benzoyl)-1-methyl-1H-pyrrol-2-ylmethyl]-2H-pyridazin-3-one;
48. 6-[5-(4-fluoro-benzoyl)-1-methyl-1H-pyrrol-2-ylmethyl]-2H-pyridazin-3-one;
49. 6-[1-methyl-5-(2-methyl-benzoyl)-1H-pyrrol-2-ylmethyl]-2H-pyridazin-3-one;
50. 6-[5-(4-ethylthio-benzoyl)-1-methyl-1H-pyrrol-2-ylmethyl]-2H-pyridazin-3-one;
51. 6-[5-(2,4-dimethyl-benzoyl)-1-methyl-1H-pyrrol-2-ylmethyl]-2H-pyridazin-3-one;
52. 6-[1-methyl-5-(4-trifluoromethyl-benzoyl)-1H-pyrrol-2-ylmethyl]-2H-pyridazin-3-one;
53. 6-[5-(4-methoxy-benzoyl)-1-methyl-1H-pyrrol-2-ylmethyl]-2H-pyridazin-3-one;
54. 6-[1-methyl-5-(4-vinyl-benzoyl)-1H-pyrrol-2-ylmethyl] -2H-pyridazin-3-one;
55. 6-[5-(4-tert-butyl-benzoyl)-1-methyl-1H-pyrrol-2-ylmethyl]-2H-pyridazin-3-one;
56. 6-[5-benzoyl-1-methyl-1H-pyrrol-2-ylmethyl]-2H-pyridazin- 3-one;
57. 6-[5-(4-bromo-benzoyl)-1-methyl-1H-pyrrol-2-ylmethyl]-2H-pyridazin-3-one;
58. 6-[1-methyl-5-(4-{1-propyl}oxy-benzoyl)-1H-pyrrol-2-ylmethyl]-2H-pyridazin-3-one;
59. 6-[1-methyl-5-(4-{2-propyl}oxy-benzoyl)-1H-pyrrol-2-ylmethyl]-2H-pyridazin-3-one;
60. 6-[5-(4-ethoxy-benzoyl)-1-methyl-1H-pyrrol-2-ylmethyl]-2H-pyridazin-3-one;
65. 6-[5-(4-acetylene-benzoyl)-1-methyl-1H-pyrrol-2-ylmethyl]-2H-pyridazin-3-one;
100. 6-[1-methyl-5-(4-methyl-benzoyl)-1H-pyrrol-2-ylmethyl]-2H-pyridazin-3-one;
106. 6-[5-(4-acetamide-benzoyl)-1-methyl-1H-pyrrol-2-ylmethyl]-2H-pyridazin-3-one;
142. 6-[1,4-dimethyl-5-(4-fluoro-benzoyl)-1H-pyrrol-2-ylmethyl]-2H-pyridazin-3-one; and 167. 6-[5-(4-chloro-benzoyl)-1-methyl-4-methylthio-1H-pyrrol-2-ylmethyl]-2H-pyridazin-3-one.

Representative compounds of Formula (Ia) where $R_1=R_2=R_3=R_4=H$, $R_5=CH_3$, $R_6=Cl$, $R_7H$, $R_8$ is a benzene ring and $R_{10}=R_{11}=H$, are as follows:

| # | $R_9$ | Melting point, °C. (solvent of crystallization) |
|---|---|---|
| 80 | $CH_3$ | 191–193 (EtOAc:hexane) |
| 81 | Cl | 182–184 (EtOAc) |
| 82 | $OCH_3$ | 162–264 ($CH_2Cl_2$:hexane) | and are named 80. 6-[4-chloro-1-methyl-5-(4-methyl-benzoyl)-1H-pyrrol-2-ylmethyl]-2H-pyridazin-3-one;
81. 6-[4-chloro-5-(4-chloro-benzoyl)-1-methyl-1H-pyrrol-2-ylmethyl]-2H-pyridazin-3-one; and
82. 6-[4-chloro-5-(4-methoxy-benzoyl)-1-methyl-1H-pyrrol-2-ylmethyl]-2H-pyridazin-3-one.

Representative compounds of Formula (Ia) where $R_1=R_2=R_3=R_7=H$, $R_8$ is a benzene ring and $R_{10}=R_{11}=H$, are as follows:

| # | $R_4$ | $R_5$ | $R_6$ | $R_9$ | Melting point, °C. (solvent of crystallization) |
|---|---|---|---|---|---|
| 9 | CN | $CH_3$ | $CH_3$ | Cl | 224–227.5 (EtOAc:hexane) |
| 18 | $CH_3$ | $CH_3$ | $CH_3$ | Cl | 194.1–196.0 (acetone) |
| 86 | H | $CH_2CH_3$ | H | $CH_3$ | 176–178 (EtOAc) |
| 95 | $CH_3$ | $CH_3$ | H | $CH_3$ | 201.8–202.3 (acetone:hexane) | and are named:

9. [5-(4-chloro-benzoyl)-1,4-dimethyl-1H-pyrrol-2-yl]-(6-oxo-1,6-dihydro-pyridazin-3-yl)acetonitrile;
18. 6-{1-[5-(4-chloro-benzoyl)-1,4-dimethyl-1H-pyrrol-2-yl]-ethyl}-2H-pyridazin-3-one;
86. 6-[1-ethyl-5-(4-methyl-benzoyl)-1H-pyrrol-2-ylmethyl]-2H-pyridazin-3-one; and
95. 6-{1-[1-methyl-5-(4-methyl-benzoyl)-1H-pyrrol-2-yl]-ethyl}-2H-pyridazin-3-one.

Representative compounds of Formula (Ia) where $R_1=R_2=R_3=R_4=H$, $R_5=CH_3$, $R_8$ is a benzene ring, and $R_{10}=R_{11}=H$, are as follows:

| # | $R_6$ | $R_7$ | $R_9$ | Melting point, °C. (solvent of crystallization) |
|---|---|---|---|---|
| 24 | $CH_3$ | Cl | Cl | 247.2–248.5 (EtOAc) |
| 25 | $CH_3$ | Br | Cl | 231.0–231.5 (EtOAc) |
| 87 | H | Cl | $CH_3$ | 212–214 (EtOAc) |
| 88 | H | Cl | $OCH_3$ | 193–195 (EtOAc) |
| 89 | $CH_3$ | Cl | H | 250–251 ($CH_2Cl_2$:acetone) |
| 107 | $SCH_3$ | H | $CH_3$ | 182–184 (EtOAc) |
| 130 | H | Br | $CH_3$ | 220–221 ($CH_2Cl_2$:EtOAc) | and are named:

24. 6-[3-chloro-5-(4-chloro-benzoyl)-1,4-dimethyl-1H-pyrrol-2-ylmethyl]-2H-pyridazin-3-one;
25. 6-[3-bromo-5-(4-chloro-benzoyl)-1,4-dimethyl-1H-pyrrol-2-ylmethyl]-2H-pyridazin-3-one;
87. 6-[3-chloro-1-methyl-5-(4-methyl-benzoyl)-1H-pyrrol-2-ylmethyl]-2H-pyridazin-3-one;
88. 6-[3-chloro-5-(4-methoxy-benzoyl)-1-methyl-1H-pyrrol-2-ylmethyl]-2H-pyridazin-3-one;
89. 6-(5-benzoyl-3-chloro-4-methyl-1H-pyrrol-2-ylmethyl)-2H-pyridazin-3-one;
107. 6-(1-methyl-5-(4-methyl-benzoyl)-4-methylthio-1H-pyrrol-2-ylmethyl)-2H-pyridazin-3-one; and
130. 6-[3-bromo-1-methyl-5-(4-methyl-benzoyl)-1H-pyrrol-2-ylmethyl]-2H-pyridazin-3-one.

Representative compounds of Formula (Ia) where $R_1=H$, $R_3=CH_3$, $R_4=H$, $R_5=R_6=CH_3$ and $R_7=H$, $R_8$ is a benzene ring, $R_9=Cl$ and $R_{10}=R_{11}=H$, are as follows:

| # | $R_2$ | Melting point, °C. (solvent of crystallization) |
|---|---|---|
| 141 | H | 219–222 (EtOAc) |
| 164 | $CH_3$ | 261–261.5 (EtOAc:hexane) | and are named:

141. 6-[5-(4-chloro-benzoyl)-1,4-dimethyl-1H-pyrrol-2-ylmethyl]-4-methyl-2H-pyridazin-3-one; and
164. 6-[5-(4-chloro-benzoyl)-1,4-dimethyl-1H-pyrrol-2-ylmethyl]-4,5-dimethyl-2H-pyridazin-3-one.

Representative compounds of Formula (Ia) where $R_1=R_2=R_3=R_4=H$, $R_5=CH_3$ and $R_7=H$, are as follows:

| # | $R_6$ | $R_8$ | $R_{12}$ | Melting point, °C. (solvent of crystallization) |
|---|---|---|---|---|
| 62 | H | 2-thienyl | H | 200–202 ($CH_2Cl_2$:hexane) |
| 63 | H | 2-thienyl | $CH_3$ | 192–193 (EtOAc:hexane) |
| 98 | H | 4-pyridyl | H | 202–203 ($CH_3OH$:EtOAc) |
| 99 | H | 3-pyridyl | H | 170–172 (THF:EtOAc) |
| 110 | H | 2-furyl | H | 198–200 (hexane:EtOAc) |
| 113 | H | 3-furyl | H | 190–191 ($CH_3OH$:EtOAc) |
| 144 | $CH_3$ | 2-thienyl | H | 188–189 ($CH_2Cl_2$:hexane) | and are named:
62. 6-[1-methyl-5-(thienyl-2-carbonyl)-1H-pyrrol-2-ylmethyl]-2H-pyridazin-3-one;
63. 6-[1-methyl-5-(5-methyl-thienyl-2-carbonyl)-1H-pyrrol-2-ylmethyl]-2H-pyridazin-3-one;
98. 6-[1-methyl-5-(pyridyl-4-carbonyl)-1H-pyrrol-2-ylmethyl]-2H-pyridazin-3-one;
99. 6-[1-methyl-5-(pyridyl-3-carbonyl)-1-methyl-1H-pyrrol-2-ylmethyl]-2H-pyridazin-3-one;
110. 6-[5-(furyl-2-carbonyl)-1-methyl-1H-pyrrol-2-ylmethyl]-2H-pyridazin-3-one;
113. 6-[5-(furyl-3-carbonyl)-1-methyl-1H-pyrrol-2-ylmethyl]-2H-pyridazin-3-one; and
144. 6-[1,4-dimethyl-5-(thienyl-2-carbonyl)-1H-pyrrol-2-ylmethyl]-2H-pyridazin-3-one.

Representative compounds of Formula (Ia) where $R_2=R_3=R_4=H$, $R_5=R_6=CH_3$, $R_7=H$, $R_8$ is a benzene ring, $R_9=Cl$, $R_{10}=R_{11}=H$, and $R_1$ is lower alkyl, halo-lower alkyl, acetyl or substituted acetyl, are as follows:

| # | $R_1$ | Melting point, °C. (solvent of crystallization) |
|---|---|---|
| 23 | $CH_3$ | 139.9–140.2 (acetone:hexane) |
| 114 | $C(O)CH_3$ | 150.5–153.3 (EtOAc) |
| 123 | $(CH_2)_2F$ | 137.5–138.0 (hexane:EtOAc) |
| 131 | $(CH_2)_2Cl$ | 134.3–135 (EtOAc:hexane) |
| 165 | $C(O)C(CH_3)_2OC(O)CH_3$ | 103–106 (hexane:EtOAc) | and are named:
23. 6-[5-(4-chloro-benzoyl)-1,4-dimethyl-1H-pyrrol-2-ylmethyl]-2-methyl-2H-pyridazin-3-one;
114. 2-acetyl-6-[5-(4-chloro-benzoyl)-1,4,-dimethyl-1H-pyrrol-2-ylmethyl]-2H-pyridazin-3-one;
123. 6-[5-(4-chloro-benzoyl)-1,4-dimethyl-1H-pyrrol-2-ylmethyl]-2-(2-fluoroethyl)-2H-pyridazin-3-one;
131. 6-[5-(4-chloro-benzoyl)-1,4-dimethyl-1H-pyrrol-2-ylmethyl]-2-(2-chloroethyl)-2H-pyridazin-3-one; and 165. acetic acid 2-{3-[5-(4-chloro-benzoyl)-1,4,-dimethyl-1H-pyrrol-2-ylmethyl]-6-oxo-6H-pyridazin-1-yl}-1,1-dimethyl-2-oxo-ethyl ester.

Representative compounds of Formula (Ia) where $R_2=R_3=R_4=H$, $R_5=R_6=CH_3$, $R_7=H$, $R_8$ is a benzene ring, $R_9=Cl$, $R_{10}=R_{11}=H$, and $R_1$ is -(CHR$_{24}$) (CH$_2$)$_n$R$_{14}$, are as follows:

| # | $R_1$ | Melting point, °C. (solvent of crystallization) |
|---|---|---|
| 118 | (CH$_2$)$_2$OH | 151–152.2 (EtOAc:hexane) |
| 122 | CH$_2$CN | 172.2–172.7 (hexane:EtOAc) |
| 124 | (CH$_2$)$_2$OCH$_3$ | 113.3–114.2 (hexane:EtOAc) |
| 126 | (CH$_2$)CCH | 167–168 (EtOAc:hexane) |
| 127 | (CH$_2$)CHCH$_2$ | 103–104.6 (hexane:EtOAc) |
| 135 | (CH$_2$)$_2$OC(O)CH$_3$ | 94.7–96 (hexane:EtOAc) |
| 136 | (CH$_2$)$_2$NHS(O)$_2$CH$_3$ | 148–149 (hexane:EtOAc) |
| 140 | (CH$_2$)$_3$OH | 126–128.3 (EtOAc:(C$_2$H$_5$)$_2$O) |
| 145 | (CH$_2$)$_2$CN | 135.2–136.3 (hexane:EtOAc) |
| 149 | CH$_2$OC(O)C(CH$_3$)$_3$ | 113.4–114.8 (hexane:EtOAc) |
| 153 | CH$_2$OH | 176–179 (CH$_3$OH) |
| 161 | CH$_2$OC(O)CH$_3$ | 126.8–127.4 (hexane:EtOAc) | and are named:

118. 6-[5-(4-chloro-benzoyl)-1,4,-dimethyl-1H-pyrrol-2-yl-methyl]-2-(2-hydroxy-ethyl)-2H-pyridazin-3-one;

122. 6-[5-(4-chloro-benzoyl)-1,4,-dimethyl-1H-pyrrol-2-yl-methyl]-2-(cyano-methyl)-2H-pyridazin-3-one;

124. 6-[5-(4-chloro-benzoyl)-1,4,-dimethyl-1H-pyrrol-2-yl-methyl]-2-(2-methoxy-ethyl)-2H-pyridazin-3-one;

126. 6-[5-(4-chloro-benzoyl)-1,4-dimethyl-1H-pyrrol-2-yl-methyl]-2-prop-2-ynyl-2H-pyridazin-3-one;

127. 2-allyl-6-[5-(4-chloro-benzoyl)-1,4-dimethyl-1H-pyrrol-2-ylmethyl]-2H-pyridazin-3one;

135. acetic acid 2-{3-[5-(4-chloro-benzoyl)-1,4,-dimethyl-1H-pyrrol-2-ylmethyl]-6-oxo-6H-pyridazin-1-yl}ethyl ester;

136. N-(2-{3-[5-(4-chloro-benzoyl)-1,4,-dimethyl-1H-pyrrol-2-ylmethyl]-6-oxo-6H-pyridazin-1-yl}-ethyl)-methanesulfonamide;

140. 6-[5-(4-chloro-benzoyl)-1,4,-dimethyl-1H-pyrrol-2-yl-methyl]-2-(3-hydroxy-1-propyl)-2H-pyridazin-3-one;

145. 6-[5-(4-chloro-benzoyl)-1,4,-dimethyl-1H-pyrrol-2-yl-methyl]-2-(2-cyano-ethyl)-2H-pyridazin-3-one;

149. trimethylacetic acid 2-{3-[5-(4-chloro-benzoyl)-1,4,-dimethyl-1H-pyrrol-2-ylmethyl]-6-oxo-6H-pyridazin-1yl}-methyl ester;

153. 6-[5-(4-chloro-benzoyl)-1,4,-dimethyl-1H-pyrrol-2-yl-methyl]-2-(hydroxy-methyl)-2H-pyridazin-3-one; and 161. acetic acid 2-{3-[5-(4-chloro-benzoyl)-1,4,-dimethyl-1H-pyrrol-2-ylmethyl]-6-oxo-6H-pyridazin-1-yl}-methyl ester.

A representative compound of Formula (Ia) where $R_2=R_3=R_4=H$, $R_5=R_6=CH_3$, $R_7=H$, $R_8$ is a benzene ring, $R_9=Cl$, $R_{10}=R_{11}=H$, and $R_1$ is -(CHR$_{24}$)(CH$_2$)$_n$C(O)R$_{15}$, is as follows:

| # | $R_1$ | Melting point, °C. (solvent of crystallization) |
|---|---|---|
| 116 | (CH$_2$)C(O)OCH$_3$ | 130.4–130.9 (EtOAc:hexane) | and is named:

116. {3-[5-(4-chloro-benzoyl)-1,4,-dimethyl-1H-pyrrol-2-ylmethyl]-6-oxo-6H-pyridazin-1-yl}-acetic acid methyl ester.

Representative compounds of Formula (Ia) where $R_2=R_3=R_4=H$, $R_5=R_6=CH_3$, $R_7=H$, $R_8$ is a benzene ring, $R_9=Cl$, $R_{10}=R_{11}=H$, and $R_1$ is -(CHR$_{24}$)(CH$_2$)$_n$C(O)NR$_{16}$R$_{17}$, are as follows:

| # | $R_1$ | Melting point, °C. (solvent of crystallization) | |
|---|---|---|---|
| 119 | CH$_2$C(O)N(CH$_3$)$_2$ | 183.7–185.2 | (CH$_3$OH) |
| 120 | CH$_2$C(O)NH$_2$ | 204–204.5 | (CH$_3$OH) |
| 125 | CH$_2$C(O)NH(CH$_3$) | 233.8–235.6 | (CH$_3$OH) |
| 128 | CH$_2$C(O)NH(CH$_2$)$_3$(CH$_3$) | 192–194 | (CH$_3$OH) |
| 132 | CH$_2$C(O)N(CH$_2$CH$_3$)$_2$ | 153–154.5 | ((C$_2$H$_5$)$_2$O:THF) |
| 157 | CH$_2$C(O)NHCH(CH$_3$)CH$_2$CH$_3$ | 199–199.8 | (hexane:EtOAc) |
| 158 | CH$_2$C(O)NHCH(CH$_3$)CH$_2$CH$_3$ chiral of Compound (157) | 198–198.8 | (hexane:EtOAc) | and are named:

119. 2-{3-[5-(4-chloro-benzoyl)-1,4,-dimethyl-1H-pyrrol-2-ylmethyl]-6-oxo-6H-pyridazin-1-yl}—N-dimethyl acetamide;

120. 2-{3-[5-(4-chloro-benzoyl)-1,4,-dimethyl-1H-pyrrol-2-ylmethyl]-6-oxo-6H-pyridazin-1-yl}-acetamide;

125. 2-{3-[5-(4-chloro-benzoyl)-1,4,-dimethyl-1H-pyrrol-2-ylmethyl]-6-oxo-6H-pyridazin-1-yl}—N-methyl acetamide;

128. 2-{3-[5-(4-chloro-benzoyl)-1,4,-dimethyl-1H-pyrrol-2-ylmethyl]-6-oxo-6H-pyridazin-1-yl}—N-butyl-acetamide;

132. 2-{3-[5-(4-chloro-benzoyl)-1,4,-dimethyl-1H-pyrrol-2-ylmethyl]-6-oxo-6H-pyridazin-1-yl}—N-diethyl-acetamide;

157. S—N-sec-butyl-2-{3-[5-(4-chloro-benzoyl)-1,4,-dimethyl-1H-pyrrol-2-ylmethyl]-6-oxo-6H-pyridazin-1-yl}-acetamide; and 158. R—N-sec-butyl-2-{3-[5-(4-chloro-benzoyl)-1,4,-dimethyl-1H-pyrrol-2-ylmethyl]-6-oxo-6H-pyridazin-1-yl}-acetamide.

Representative compounds of Formula (Ia) where $R_2=R_3=R_4=H$, $R_5=R_6=CH_3$, $R_7=H$, $R_8$ is a benzene ring, $R_9=Cl$, $R_{10}=R_{11}=H$, and $R_1$ is —CHR$_{24}$R$_{18}$, are as follows:

| # | $R_1$ | Melting point, °C. (solvent of crystallization) |
|---|---|---|
| 117 | 3,4-dichlorobenzyl | 147.9–149 (hexane:EtOAc) |
| 121 | benzyl | 133.2–134.2 (hexane:EtOAc) |

| # | R₁ | Melting point, °C. (solvent of crystallization) |
|---|---|---|
| 129 | 4-fluorobenzyl | 162.5–163.3 (hexane:EtOAc) |
| 133 | 4-chlorobenzyl | 133.8–135.1 (hexane:EtOAc) |
| 134 | 4-methylbenzyl | 127–128 (hexane:EtOAc:ether) |
| 137 | 2-fluorobenzyl | 125.5–126.2 (hexane:EtOAc:ether) |
| 138 | 4-cyanobenzyl | 147–148.3 (hexane:CH₂Cl₂) |
| 139 | 3-fluorobenzyl | 141.7–142.8 (hexane:EtOAc) |
| 146 | 3-cyanobenzyl | 137.2–138.6 (hexane:EtOAc) |
| 147 | 2-cyanobenzyl | 141.1–141.9 (hexane:EtOAc) |
| 151 | 2,6-dimethylbenzyl | 57.0–60.5 (hexane:EtOAc) |
| 152 | 2,6-dichlorobenzyl | 59.0–62.5 (hexane:EtOAc) |
| 156 | 3-pyridyl | 156.5–157.9 (EtOAc) |
| 168 | 4-methoxybenzyl | 134.9–136.5 (hexane:EtOAc) | and are named:

117. 6-[5-(4-chloro-benzoyl)-1,4,-dimethyl-1H-pyrrol-2-yl-methyl]-2-(3,4-dichlorobenzyl)-2H-pyridazin-3-one;

121. 2-benzyl-6-[5-(4-chloro-benzoyl)-1,4,-dimethyl-1H-pyrrol-2-ylmethyl]-2H-pyridazin-3-one;

129. 6-[5-(4-chloro-benzoyl)-1,4,-dimethyl-1H-pyrrol-2-yl-methyl]-2-(4-fluorobenzyl)-2H-pyridazin-3-one;

133. 6-[5-(4-chloro-benzoyl)-1,4,-dimethyl-1H-pyrrol-2-yl-methyl]-2-(4-chlorobenzyl)-2H-pyridazin-3-one;

134. 6-[5-(4-chloro-benzoyl)-1,4,-dimethyl-1H-pyrrol-2-yl-methyl]-2-(4-methylbenzyl)-2H-pyridazin-3-one;

137. 6-[5-(4-chloro-benzoyl)-1,4,-dimethyl-1H-pyrrol-2-yl-methyl]-2-(2-fluorobenzyl)-2H-pyridazin-3-one;

138. 4-{3-[5-(4-chloro-benzoyl)-1,4,-dimethyl-1H-pyrrol-2-ylmethyl]-6-oxo-6H-pyridazin 1-ylmethyl}-benzonitrile;

139. 6-[5-(4-chloro-benzoyl)-1,4,-dimethyl-1H-pyrrol-2-yl-methyl]-2-(3-fluorobenzyl) 2H-pyridazin-3-one;

146. 3-{3-[5-(4chloro-benzoyl)-1,4,-dimethyl-1H-pyrrol-2-ylmethyl]-6-oxo-6H-pyridazin-1-ylmethyl}-benzonitrile;

147. 2-{3-[5-(4-chloro-benzoyl)-1,4,-dimethyl-1H-pyrrol-2-ylmethyl]-6-oxo-6H-pyridazin-1-ylmethyl}-benzonitrile;

151. 6-[5-(4-chloro-benzoyl)-1,4,-dimethyl-1H-pyrrol-2-yl-methyl]-2-(2,6-dimethylbenzyl)-2H-pyridazin-3-one;

152. 6-[5-(4-chloro-benzoyl)-1,4,-dimethyl-1H-pyrrol-2-yl-methyl]-2-(2,6-dichlorobenzyl)-2H-pyridazin-3-one;

156. 6-[5-(4-chloro-benzoyl)-1,4,-dimethyl-1H-pyrrol-2-yl-methyl]-2-(3-pyridyl)-2H-pyridazin-3-one; and 168. 6-[5-(4-chloro-benzoyl)-1,4,-dimethyl-1H-pyrrol-2-yl-methyl]-2-(4-methoxybenzyl)-2H-pyridazin-3-one.

The invention also relates to a family of compounds of Formula (Ib) having the structure:

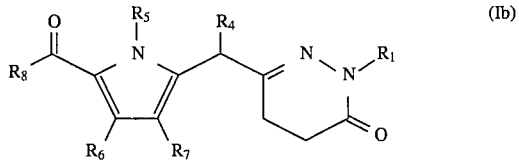

(Ib)

wherein $R_1$ and $R_4$ to $R_8$ are as defined above; and the pharmaceutically acceptable salts thereof.

Representative compounds of Formula (Ib), where $R_1=R_4=R_7=R_{10}=R_{11}=H$ and $R_8$ is a benzene ring, are as follows:

| # | R₅ | R₆ | R₉ | Melting point, °C. (solvent of crystallization) |
|---|---|---|---|---|
| 94 | CH₃ | CH₃ | Cl | 198–201 (isopropanol) |
| 102 | CH₃ | H | CH₃ | 171–172 (CH₂Cl₂:CH₃OH) | and are named:

94. 6-[5-(4-chloro-benzoyl)-1,4-dimethyl-1H-pyrrol-2-ylmethyl]-4,5-dihydro-2H-pyridazin-3-one; and 102. 6-[1-methyl-5-(4-methyl-benzoyl)-1H-pyrrol-2-ylmethyl]-4,5-dihydro-2H-pyridazin-3-one.

The invention also relates to a family of compounds of Formula (II) having the structure:

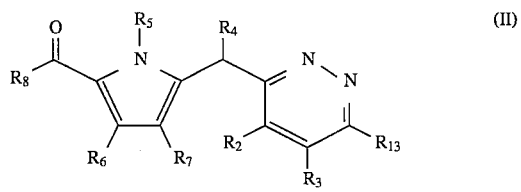

(II)

wherein: $R_2$ to $R_8$ are as defined above and $R_{13}$ is lower alkoxy, mercapto, lower alkylthio, —NR₂₁R₂₂ or —O-(CH₂)ₘ—NR₂₁R₂₂; where m is an integer from 1 to 6, $R_{21}$ is —H or lower alkyl and $R_{22}$ is —H or lower alkyl, and where $R_{21}$ and $R_{22}$ may be taken together with N to form a ring of three to five carbon atoms which may include one member that is —O—, —S—, or —N(R₂₃)— where R₂s is —H or lower alkyl; and the pharmaceutically acceptable salts thereof.

Representative compounds of Formula (II), where $R_2=R_3=R_4=H$, $R_5=R_6=CH_3$, $R_7=H$, $R_8$ is a benzene ring, $R_9=Cl$ and $R_{10}=R_{11}=H$, are as follows:

| # | R₁₃ | Melting point, °C. (solvent of crystallization) |
|---|---|---|
| 19 | OCH₃ | 152.5–153.5 (hexane:EtOAc) |
| 20 | OCH(CH₃)₂ | 124.9–126.3 (hexane:EtOAc) |
| 21 | OCH₂CH₃ | 132.8–133.7 (hexane:EtOAc) |
| 22 | O(CH₂)₂-morpholino (HCl salt) | 132.8–133.5 (EtOAc) |
| 96 | NHNH₂ | 159–161 (water:DMSO) |
| 103 | NH₂ | 206.8–209 (CH₃CN:DMF:water) |
| 169 | SH | 220.4–222.4 (acetone:hexane) | and are named:

19. (4-chloro-phenyl)-[5-(1,6-dihydro-6-methoxy-pyridazin-3-ylmethyl)-1,3-dimethyl-1H-pyrrol-2-yl]-methanone;

20. (4-chloro-phenyl)-{5-[1,6-dihydro-6-(2-propyl)oxy-pyridazin-3-ylmethyl]-1,3-dimethyl-1H-pyrrol-2-yl}-methanone;

21. (4-chloro-phenyl)-[5-(6-ethoxy-1,6-dihydro-pyridazin-3-ylmethyl]-1,3-dimethyl-1H-pyrrol-2-yl-methanone;

22. HCl salt of (4-chloro-phenyl)-{1,3-dimethyl-5-[6-(2-morpholin-4-yl-ethoxy)-1,6-dihydro-pyridazin-3-ylmethyl]-1H-pyrrol-2-yl}-methanone;

96. (4-chloro-phenyl)-[5-(6-hydrazino-1,6-dihydro-pyridazin-3-ylmethyl)-1,3-dimethyl-1H-pyrrol-2-yl]-methanone;

103. (4-chloro-phenyl)-[5-(6-amino-1,6-dihydro-pyridazin-3-ylmethyl)-1,3-dimethyl-1H-pyrrol-2-yl]-methanone; and 169. (4-chloro-phenyl)-[5-(1,6-dihydro-6-mercapto-pyridazin-3-ylmethyl)-1,3-dimethyl-1H-pyrrol-2-yl]-methanone.

The invention also relates to a family of compounds of Formula (III) having the structure:

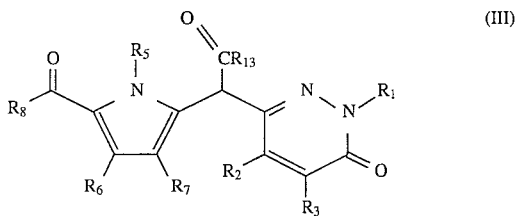

(III)

wherein: $R_1$ to $R_3$, $R_5$ to $R_8$, and $R_{13}$ are as defined above; and the pharmaceutically acceptable salts thereof.

Representative compounds of Formula (III), where $R_1=R_2=R_3=H$, $R_5=R_6=CH_3$, $R_7=H$, $R_8$ is a benzene ring, $R_9=Cl$ and $R_{10}=R_{11}=H$, are as follows:

| # | $R_{13}$ | Melting point, °C. (solvent of crystallization) |
|---|---|---|
| 27 | OH | not characterized |
| 28 | ONa (Na salt of Compound (27)) | 189 (CH$_3$OH:H$_2$O) |
| 29 | O(CH$_2$)$_2$-morpholino (HCl salt) | 162.5 (EtOAc:hexane) |
| 112 | OCH$_3$ | 216–217.5 (EtOAc:hexane) | and are named:
27. [5-(4-chloro-benzoyl)-1,4-dimethyl-1H-pyrrol-2-yl]-(6-oxo-1,6-dihydro-pyridazin-3-yl)-acetic acid;
28. sodium salt of 6-[5-(4-chloro-benzoyl)-1,4-dimethyl-1H-pyrrol-2-yl]-(6-oxo-1,6-dihydro-pyridazin-3-yl)-acetic acid;
29. HCl salt of [5-(4-chloro-benzoyl)-1,4-dimethyl-1H-pyrrol-2-yl]-(6-oxo-1,6-dihydro-pyridazin-3-yl)-acetic acid 2-morpholin-4-yl-ethyl ester; and
112. [5-(4-chloro-benzoyl)-1,4-dimethyl-1H-pyrrol-2-yl]-(6-oxo-1,6-dihydropyridazin-3-yl)-acetic acid methyl ester.

Studies conducted in animal models indicate that compounds of the invention exhibit the anti-inflammatory effects associated with NSAIDs, but do not exhibit the GI irritant effects common with such drugs. Similarly, these compounds have analgesic properties. These compounds are useful in the treatment of inflammation and pain caused by, for example, arthritis, gout and autoimmune disorders such as, by way of example and not limitation, systemic lupus erythematosus, rheumatoid arthritis and type I diabetes. These compounds are also useful in the treatment of cancer. The term "treatment" means any treatment of a disease in a mammal, including preventing the condition or disease by preventing the development of clinical symptoms of the disease; arresting the further progression of clinical symptoms; and relieving the condition or disease by causing the regression of clinical symptoms.

Most compounds of Formula (Ia) and (Ib) are themselves orally active selective inhibitors of prostaglandin G/H synthase II ("COX II"). However, some compounds of Formula (Ia) and (Ib) can be prodrugs that, when administered to a patient, become converted in the body to the therapeutically active compounds having Formula (Ia) or (Ib). In addition, Compounds of Formula (II) and Formula (III) may be prodrugs of the therapeutically active compounds of Formula (Ia) and (Ib).

The preferred compounds of Formula (Ia) have the following substituents. Preferably, $R_1$ is —H, -(CHR$_{24}$)(CH$_2$)$_n$R$_{14}$ or —CHR$_{24}$R$_{18}$. More preferably, $R_1$ is —H, —CH$_2$CN or —CHR$_{24}$R$_{18}$, where $R_{18}$ is a benzene ring and $R_{19}$ and $R_{20}$ are independently selected from the group consisting of —CN, halo and lower alkyl, most preferably —CN, —Cl or —CH$_3$. Even more preferably, $R_1$ is —H. $R_2$, $R_3$ and $R_4$ are preferably —H. $R_5$ is preferably lower alkyl; more preferably, $R_5$ is —CH$_3$. $R_6$ is preferably lower alkyl; more preferably, $R_6$ is —CH$_3$. Preferably, $R_7$ is —H, halo or lower alkyl. More preferably, $R_7$ is —H, —Cl or —CH$_3$. Even more preferably, $R_7$ is —H. Preferably, $R_8$ is a benzene ring, where $R_9$ is halo, lower alkyl, lower alkoxy, lower alkylthio, or lower alkene, and $R_{10}$ and $R_{11}$ are —H. More preferably, $R_9$ is —Cl, —Br, —SCH$_3$, or —CHCH$_2$, with —Cl being the most preferred.

The preferred compounds of Formula (Ib) have the following substituents. Preferably, $R_1$ is —H, -(CHR$_{24}$)(CH$_2$)$_n$R$_{14}$ or —CHR$_{24}$R$_{18}$. More preferably, $R_1$ is —H, —CH$_2$CN or —CHR$_{24}$R$_{18}$, where $R_{18}$ is a benzene ring and $R_{19}$ and $R_{20}$ are independently selected from the group consisting of —CN, halo and lower alkyl, most preferably —CN, —Cl or —CH$_3$. Even more preferably, $R_1$ is —H. $R_4$ is preferably —H. $R_5$ is preferably lower alkyl; more preferably, $R_5$ is —CH$_3$. $R_6$ is preferably lower alkyl; more preferably, $R_6$ is —CH$_3$. Preferably, $R_7$ is —H, halo or lower alkyl. More preferably, $R_7$ is —H, —Cl or —CH$_3$. Even more preferably, $R_7$ is —H. Preferably, $R_8$ is a benzene ring, where $R_9$ is halo, lower alkyl, lower alkoxy, lower alkylthio, or lower alkene, and $R_{10}$ and $R_{11}$ are —H. More preferably, $R_9$ is —Cl, —Br, —SCH$_3$, or —CHCH$_2$, with —Cl being the most preferred.

The preferred compounds of Formula (II) have the following substituents. $R_2$, $R_3$ and $R_4$ are preferably —H. $R_5$ is preferably lower alkyl; more preferably, $R_5$ is —CH$_3$. $R_6$ is preferably lower alkyl; more preferably, $R_6$ is —CH$_3$. Preferably, $R_7$ is —H, halo or lower alkyl. More preferably, $R_7$ is —H, —Cl or —CH$_3$. Even more preferably, $R_7$ is —H. Preferably, $R_8$ is a benzene ring, where $R_9$ is halo, lower alkyl, lower alkoxy, lower alkylthio, or lower alkene, and $R_{10}$ and $R_{11}$ are —H. More preferably, $R_9$ is —Cl, —Br, —SCH$_3$, or —CHCH$_2$, with —Cl being the most preferred. $R_{13}$ is preferably lower alkoxy.

The preferred compounds of Formula (III) have the following substituents. Preferably, $R_1$ is —H, -(CHR$_{24}$)(CH$_2$)$_n$R$_{14}$ or —CHR$_{24}$R$_{18}$. More preferably, $R_1$ is —H, —CH$_2$CN or —CHR$_{24}$R$_{18}$, where $R_{18}$ is a benzene ring and $R_{19}$ and $R_{20}$ are independently selected from the group consisting of —CN, halo and lower alkyl, most preferably —CN, —Cl or —CH$_3$. Even more preferably, $R_1$ is —H. $R_2$ and $R_3$ are preferably —H. $R_5$ is preferably lower alkyl; more preferably, $R_5$ is —CH$_3$. $R_6$ is preferably lower alkyl; more preferably, $R_6$ is —CH$_3$. Preferably, $R_7$ is —H, halo or lower alkyl. More preferably, $R_7$ is —H, —Cl or —CH$_3$. Even more preferably, $R_7$ is —H. Preferably, $R_8$ is a benzene ring, where $R_9$ is halo, lower alkyl, lower alkoxy, lower alkylthio, or lower alkene, and $R_{10}$ and $R_{11}$ are —H. More preferably, $R_9$ is —Cl, —Br, —SCH$_3$, or —CHCH$_2$, with —Cl being the most preferred. $R_{13}$ is preferably lower alkoxy.

When $R_1$ is hydrogen, the compounds of this invention can also undergo tautomerism where compounds with an =O group on the pyridazinone ring exist in equilibrium with compounds having an —OH group. However the equilibrium lies in favor of the keto form. For example, this invention encompasses not only the compounds of Formula (Ia), but also the tautomer forms having the formula:

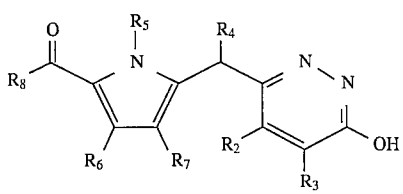

and the compounds of Formula (III) can exist in the tautomer form:

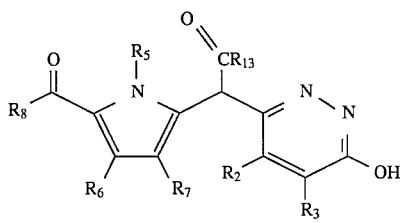

In addition, some compounds of Formula (II) can exist in the tautomer forms. For example, Compound (169), where $R_{13}$ is —SH can also exist in the tautomeric thioxo form.

Compounds of Formula (Ia), (Ib), (II) and (III) can be made, for example, by the general reaction schemes shown below. The starting materials and reagents used in preparing these compounds are either available from commercial suppliers such as Aldrich Chemical Co. or are prepared by methods known to those skilled in the art following procedures set forth in references such as, "Fieser and Fieser's Reagents for Organic Synthesis", Volumes 1–15 (John Wiley and Sons, 1991); "Rodd's Chemistry of Carbon Compounds", Volumes 1–5 and Supplementals (Elsevier Science Publishers, 1989); and "Organic Reactions", Volumes 1–40 (John Wiley and Sons, 1991). These schemes are merely illustrative of some methods by which the compounds of the present invention can be synthesized and various modifications to these schemes can be made, and will be suggested to one skilled in the art.

The term "suitable solvent" means an organic solvent that is inert under the conditions of the reaction being described. Typical suitable solvents include, by way of example and not limitation, benzene, toluene, acetonitrile, tetrahydrofuran, dimethylformamide, chloroform, methylene chloride, diethyl ether, methanol, pyridine, N-methyl-pyrrolidone, ethanol, acetic acid, xylene, 1,2-dichloroethane and the like.

Scheme A is used to synthesize compounds of Formula (Ia).

SCHEME A

Step 1

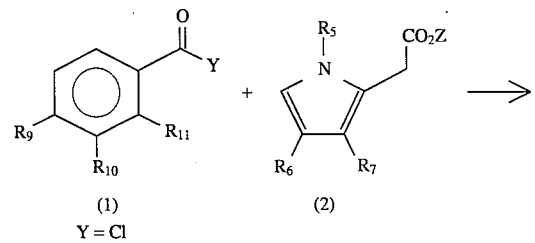

-continued
SCHEME A

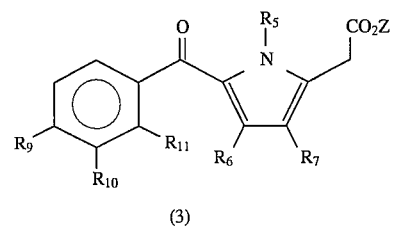

Step 2

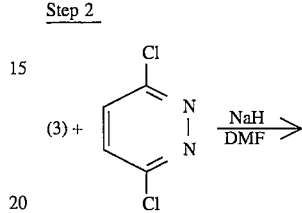

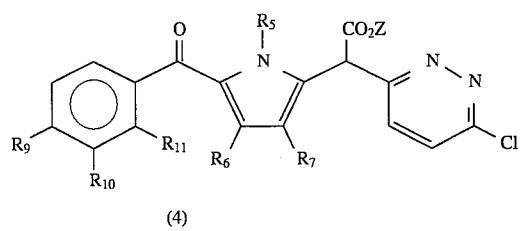

Step 3a

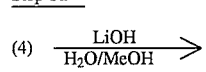

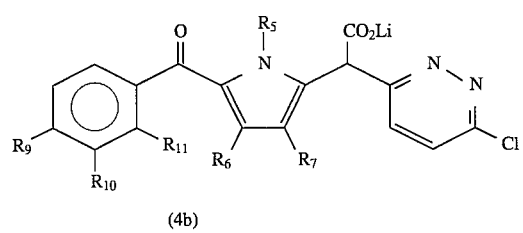

Step 3b

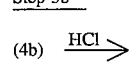

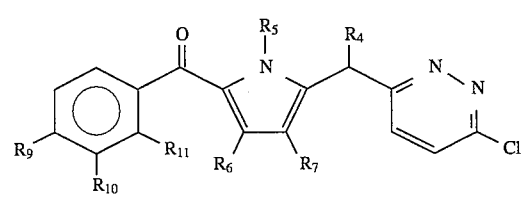

(5)
$R_4 = H$

-continued
SCHEME A

Step 4a (5) $\xrightarrow{\text{NaOAc}}{\text{HOAc}}$

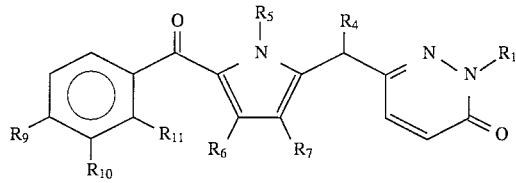

(6)
$R_1 = R_4 = H$

Step 4b (6) $\xrightarrow{R_1X}{Cs_2CO_3}$

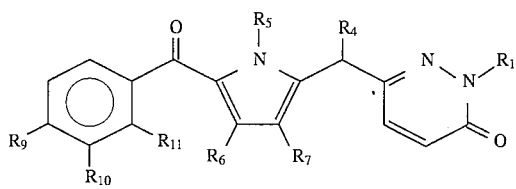

(7)
$R_1$ = alkyl
$R_4$ = H

Step 1 is an acylation reaction of Compound (2), the pyrrole. Compound (1) is preferably a benzoyl chloride (Y=Cl) or N,N-dimethylbenzamide (Y=N(CH$_3$)$_2$). Preferably, Z=CH$_3$ or CH$_2$CH$_3$, R$_5$=CH$_3$ or CH$_2$CH$_3$, R$_6$=H or CH$_3$, R$_7$=H and R$_{10}$=R$_{11}$=H. When a benzoyl chloride is used, no additional reagents are needed as the reaction proceeds with only the addition of heat. When N,N-dimethylbenzamide is used, suitable reagents include, without limitation, phosphorous oxychloride, phosphorous pentachloride and oxalyl chloride. For example, using Compound (1) where Y=N(CH$_3$)$_2$, R$_9$=CH$_3$ and R$_{10}$=R$_{11}$=H, Compound (1) is reacted with POCl$_3$ in a suitable solvent such as dichloroethane, followed by the addition of Compound (2) in a similar solvent, where Z=CH$_2$CH$_3$ and R$_5$=R$_6$=CH$_3$. This is followed by the addition of sodium acetate. Alternately, Compound (1) where Y=Cl, R$_9$=OCH$_3$ and R$_{10}$=R$_{11}$=H, and Compound (2) where Z=CH$_2$CH$_3$, R$_5$=CH$_3$ and R$_6$=H, can be reacted in xylene.

Compound (2) can be synthesized in numerous ways. The process described by Stahley, et al., *J. Org. Chem* 48:4423 (1983) is useful for synthesizing Compound (2) where Z=CH$_2$CH$_3$ and R$_5$=R$_6$=CH$_3$.

Preferably, Compound (3) is an ester (Z=CH$_3$ or CH$_2$CH$_3$). However, Compound (3) may be a sodium salt (Z=Na). In the latter case, Compound (3) is treated with an alkylating reagent such as CH$_3$I to convert the compound to its ester form (Z=CH$_3$) prior to Step 2. Suitable solvents for this reaction include, for example, dimethylformamide and N-methyl pyrrolidone. Compounds having the general formula of Compound (3) are also commercially available, for example the sodium salt of zomepirac (Compound (11)) in Example 1) and tolmetin (Compound (10) in Example 17) are available from Sigma Chemical Company. Therefore, depending upon the desired Z, R$_5$ to R$_7$ and R$_9$ to R$_{11}$ substituents, Step 1 can be eliminated if Compound (3), with the desired Z, R$_5$ to R$_7$ and R$_9$ to R$_{11}$ substituents, is commercially available.

Step 2 is a heteroarylation reaction of Compound (3) with sodium hydride and 3,6-dichloropyridazine in an appropriate solvent, for example, dimethylformamide or N-methyl pyrrolidone.

Step 3a involves a hydrolysis reaction. Suitable hydrolysis reagents include, without limitation, lithium hydroxide, sodium hydroxide, potassium hydroxide and barium hydroxide. Step 3b is a decarboxylation reaction. Suitable decarboxylation reagents include, without limitation, hydrochloric acid, acetic acid and sulfuric acid.

Step 4a is a hydrolysis reaction and suitable hydrolysis reagents include, without limitation, sodium acetate, sodium acetate trihydrate, acetic acid, lithium hydroxide, sodium hydroxide, potassium hydroxide.

Scheme A, Steps 1 through 4a was used to synthesize numerous compounds having the structure of Formula (Ia). These include, for example, Compounds (16) and (30) through (60).

Step 4b is an alkylation reaction using R$_1$X, where R$_1$ is as defined above, and X is any leaving group, including without limitation, halo groups, methane sulfonate, p-toluene sulfonate. For example, R$_1$X can be a halo-alkyl, a benzyl halide, an ethyl halo acetate, and so forth. Alkylation is done in the presence of a base such as cesium carbonate, sodium hydride and potassium carbonate.

Scheme A, Steps 1 through 4b was used to synthesize Compound (23), for example.

Alternately, Step 4b is an acylation reaction using an acid chloride such as acetylchloride, and a suitable base, for example, pyridine, triethylamine, tributylamine, or N-methyl morpholine. This acylation step is used to synthesize compounds where R$_1$ is an acetyl or substituted acetyl, and was used to synthesize Compounds (114) and (165), for example.

Still another alternate way of performing Step 4b involves combining Compound (6) with formaldehyde in a suitable solvent such as methanol, ethanol or isopropanol, for example. This is used to synthesize compounds where R$_1$ is hydroxy-methyl, and was used to synthesize Compound (153), for example.

Scheme B, below, is used to synthesize compounds of Formula (Ia) where R$_4$ is a lower alkyl.

SCHEME B

Steps 1-3 as described in Scheme A, Steps 1-3b.

Step 4a (5) $\xrightarrow{\text{1) base}}{\text{2) R}_4\text{X}}$

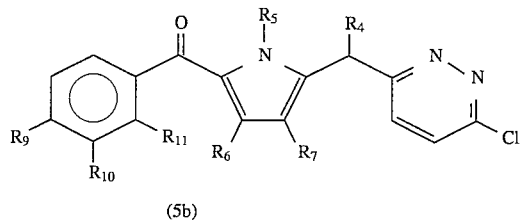

(5b)

-continued
SCHEME B

Step 4b (5b) $\xrightarrow{\text{NaOAc}}{\text{HOAc}}$

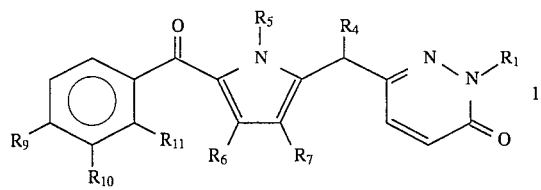

(8)
R$_1$ = H
R$_4$ = alkyl

Step 4a of Scheme B involves an alkylation reaction. The alkylation reagent is R$_4$X, where R$_4$ is as defined above and X is any leaving group, as is defined above in Scheme A, Step 4b. Suitable bases for the alkylation reaction include those listed above in Scheme A, Step 4b. Step 4b of Scheme B involves hydrolysis of the chloropyridazine and suitable reagents include those listed above for Scheme A, Step 4a.

Scheme B was used to synthesize Compound (18), for example.

Scheme C, below, is used to synthesize compounds of Formula (Ia) where R$_4$ is cyano (—CN).

SCHEME C

Step 1

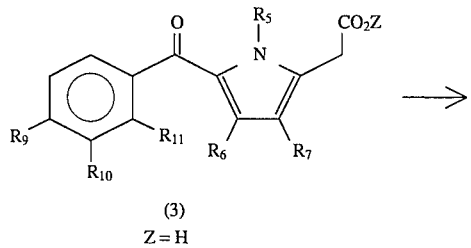

(3)
Z = H

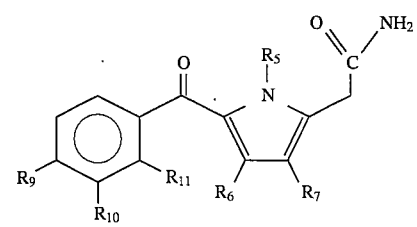

(90)

Step 2

(90) $\longrightarrow$

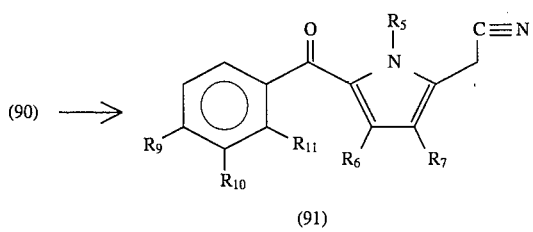

(91)

-continued
SCHEME C

Step 3 as described in Scheme A, Step 2.

(91) $\xrightarrow{\text{NaH}}$ 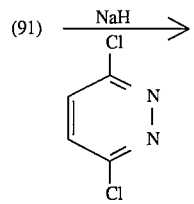

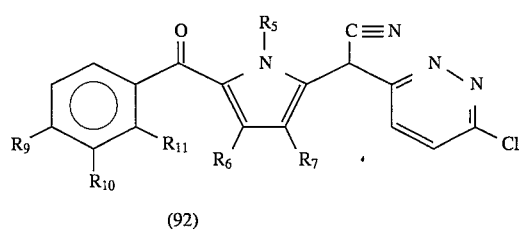

(92)

Step 4 as described in Scheme A, Step 4a.

(92) $\xrightarrow{\text{NaOAc}}{\text{HOAc}}$

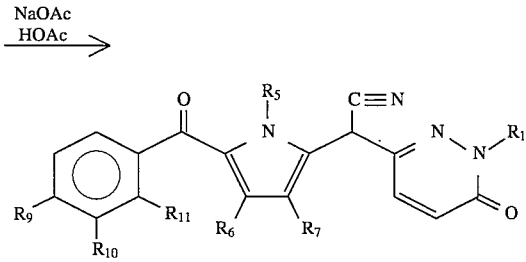

(93)

Steps 1 and 2 involve a well established conversion of a carboxyl group to an amide. Step 1 is an amide bond formation reaction and involves reacting Compound (3) with a reagent such as ammonia.

Step 2 involves dehydration of the amide to the nitrile and involves reacting Compound (90) with a dehydrating reagent such as acetic anhydride.

Scheme C was used to synthesize Compound (9), for example.

Scheme D, below, is used to synthesize compounds of Formula (Ib).

SCHEME D

Steps 1–4 as described for Scheme A, Steps 1–4a.

Step 5

(6) $\longrightarrow$

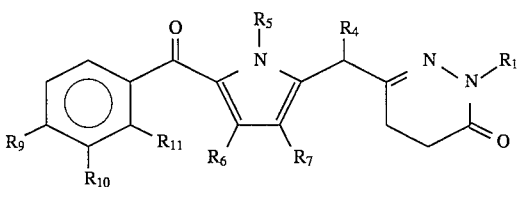

(101)

Step 5 is a reduction step and a suitable reagent is zinc in acetic acid.

Scheme D was used to synthesize Compound (102), for example.

Scheme E, below, is used to synthesize compounds of Formula (II).

SCHEME E

Steps 1–3 as described in Scheme A, Steps 1–3b.

Step 4

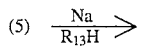

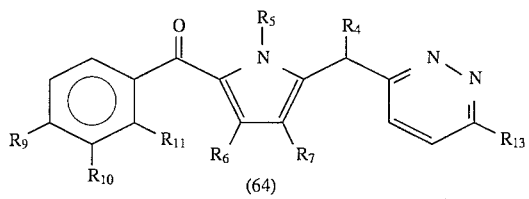

Step 4 is an etherification step and $R_{13}H$ is an alcohol such as methanol, isopropanol, ethanol and morpholino ethanol. Sodium or sodium hydride can be used.

Scheme E was used to synthesize Compounds (19) through (22), for example.

Scheme F, below, is used to synthesize compounds of Formula (III):

SCHEME F

Steps 1–2 as described in Scheme A, Steps 1–2.

Step 3:

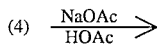

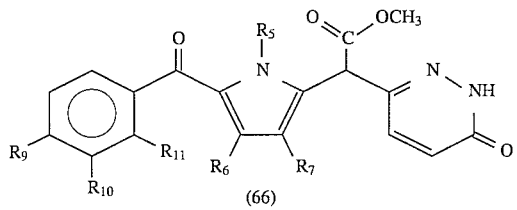

Step 4:

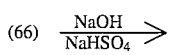

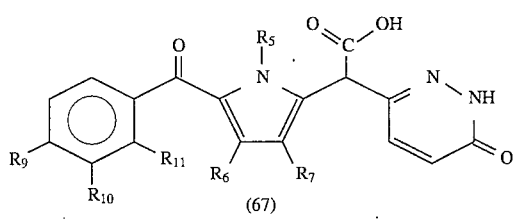

Step 5:

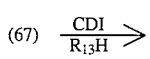

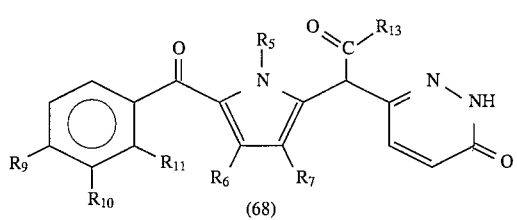

Step 3 is a hydrolysis reaction using sodium acetate in acetic acid. Step 4 is a hydrolysis reaction and suitable reagents include sodium hydroxide, lithium hydroxide and potassium hydroxide. Step 5 is an esterification reaction and $R_{13}H$ is an alcohol as described in Scheme E, Step 4. Suitable esterifying agents include, for example, carbonyldiimidazole, dicyclohexylcarbodiimide, and diisopropylcarbodiimide.

Scheme F, Steps 1–4 can be followed by a step involving the reaction of Compound (67) with a material such as sodium bicarbonate to provide the salt form of the drug, which has better water solubility. This was done to synthesize Compound (28), for example. Scheme F, Steps 1–5 was used to synthesize Compound (29), for example.

There are numerous ways to modify substituents on compounds formed by the general Schemes described above. For example, halogenation of the compounds formed in the above Schemes can also be readily accomplished. One method converts the $R_7$ substituent on the pyrrole from a hydrogen to a halo group. A compound such as Compound (6) is reacted with a halogenating agent in a suitable solvent to halogenate the pyrrole. Suitable halogenating agents include 1,3-dihalo-5,5-dimethyl hydantoin, N-chlorosuccinimide, and N-bromosuccinimide. Suitable solvents include, acetone, tetrahydrofuran and dimethylformamide. This method was used to synthesize Compounds (24), (25) and (87) through (89).

Compounds of the invention having the $R_6$ substituent as a halo group, can readily be synthesized. Compound (2) in the aforementioned Schemes can be a halogenated pyrrole where $R_6$ is a halo group. This halogenated pyrrole can be made by a synthesis such as that described in Example 15 for Compound (79). This method was also used to synthesize Compounds (80) through (82), for example.

Compounds of the invention having a lower alkylthio group as substituent $R_6$ or $R_7$, can also be synthesized. In any of the aforementioned Schemes, Compounds (1) and (2) can be reacted by the method described in Muchowski, et al., J. Med. Chem 32:1202 (1989):

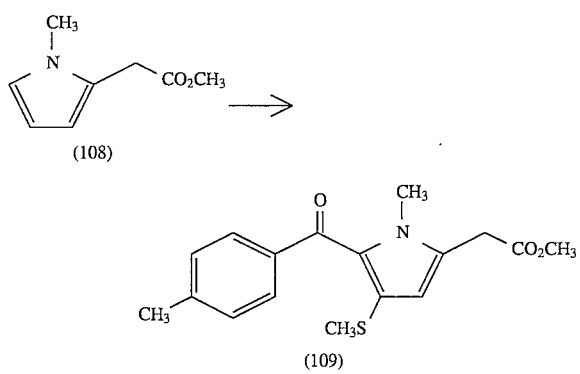

This step would then be followed by any of the subsequent steps described in the Schemes above. This method was used to synthesize the Compound (107), for example.

Compound (2) in any of the above Schemes can also be an alkylated pyrrole where $R_5$ is a lower alkyl group, other than methyl to provide a compound of the invention where $R_5$ is a lower alkyl group, other than methyl. This alkylated pyrrole can be made by a synthesis such as that done in Example 16 for Compound (85) having the following substituents: $R_5$=$CH_2CH_3$, $R_6$=H and Z=$CH_2CH_3$. This method of using an alkylated pyrrole in the above Schemes was used to synthesize Compound (86), for example.

The Schemes above illustrate the synthesis of compounds where $R_8$ is a benzene group. This is for illustrative purposes and is not intended to limit the Schemes in any manner, since $R_8$ can also be a thienyl, furyl or pyridyl group. The Schemes can be easily modified by using a thienyl-carbonyl chloride or thienyl-dimethylamide, furyl-carbonyl chloride or furyl-dimethylamide, and pyridyl-carbonyl chloride or pyridyl-dimethylamide, respectively, as starting materials instead of a benzoyl chloride or N,N-dimethylbenzamide, Compound (1). For example, thienyl-carbonyl chloride was used as a starting material to synthesize Compounds (62) and (63), for example.

Compounds where $R_9$ is an alkyne can be readily synthesized by converting a $R_9$ halo group to an alkyne by a coupling reaction with an appropriate acetylene compound such as trimethylsilylacetylene and other reagents such as palladium diacetate, $PPh_3$ in triethylamine, and acetonitrile, followed by reaction with potassium carbonate. This is described in Example 20 for the synthesis of Compound (65).

Compounds where $R_9$ is a lower alkyl amido are also readily synthesized. In any one of the aforementioned Schemes, starting materials of the formula of Compound (3) can be synthesized with $R_9$ being a nitro group. The resulting compound is then reacted with an agent such as nickel boride followed by acetic anhydride to convert the nitro group to an amino groups, which is then converted to a lower alkyl amido group. This method was used to synthesize the starting material Compound (105) in Example 21. Compound (105) was then used to synthesize Compound (106), for example.

Isolation and purification of the above compounds and their intermediates can be done by any suitable separation or purification procedure such as, for example, filtration, extraction, crystallization, column chromatography, preparative high pressure liquid chromatography, thin-layer chromatography, thick-layer chromatography, or a combination of these procedures. Specific illustrations of suitable separation and isolation procedures can be had by reference to the examples set forth below. However, other equivalent separation or isolation procedures can also be used and will be suggested to one skilled in the art.

This invention also relates to pharmaceutical compositions containing a therapeutically effective amount of a compound of Formula (Ia), (Ib), (II) or (III), mixed with at least one pharmaceutically acceptable excipient.

The compounds of the present invention may exist in several crystal phases or polymorphs, which in turn, may exist in both the anhydrous and hydrate states. For example, Compound (16) has been found to exist in at least three anhydrous crystal forms and two hydrates. One skilled in the art can evaluate the factors involved to decide which phase or state is preferred for a particular pharmaceutical formulation or mode of administration. These factors include, by way of illustration and not limitation, stability, performance in chemical manufacturing, performance in biostudies (bioavailability), performance in pharmaceutical operation (blending, granulation, high speed tablet and capsule machines) and product stability (interaction with excipients).

The compounds of this invention can be incorporated into a pharmaceutical composition either in the hydrated or anhydrous form. Preferably the compound is in its hydrated form.

The term "therapeutically effective amount" refers to the amount of the compound which, when administered to a mammal in need thereof, is sufficient to effect treatment as an anti-inflammatory agent and/or analgesic agent. The amount that constitutes a "therapeutically effective amount" will vary depending on the compound, the condition or disease and its severity, and the mammal to be treated, its weight, age, etc., but may be determined routinely by one of ordinary skill in the art with regard to contemporary knowledge and to this disclosure.

This invention also relates to a method of use of compounds of Formula (Ia), (Ib), (II) and (III) as anti-inflammatory agents to treat inflammation and pain by administering to a mammal in need of such treatment a therapeutically effective amount of the compound or a pharmaceutically acceptable salt thereof. This method also is useful to treat cancer.

A key aspect of this invention is that the compounds of Formula (Ia), (Ib), (II) and (III) are useful as anti-inflammatory agents but do not exhibit the adverse gastrointestinal ("GI") side effects commonly associated with NSAIDs. Similarly, it is expected that these compounds will not exhibit adverse renal side effects. This has been shown in Example 38 for Compound (16).

In another aspect, this invention provides compositions useful in the treatment of the above conditions comprising a therapeutically effective amount of a compound of Formula (Ia), (Ib), (II) or (III) and a pharmaceutically acceptable excipient, such as are described below.

As mentioned above, the compounds of the present invention are GI sparing NSAIDs. NSAIDs operate through the inhibition of COX I and COX II, the enzymes which catalyze the oxygenation and cyclization of arachidonic acid to prostaglandin $H_2$. COX I is expressed in most tissues, including the GI tract and the kidney, while COX II expression has been found in inflamed cells and tissues. We believe that specific and selective inhibitors of COX II can possess the desirable therapeutic effects of NSAIDs, such as anti-inflammatory action and some analgesic traits, without exhibiting adverse side effects to the GI tract and kidneys.

To find NSAIDs highly selective for COX II, compounds are screened and structure activity selectivity relationships defined. Determination of tertiary structure of enzyme inhibitor complexes also facilitates discovery of potent and selective inhibitors. An appreciable supply of purified human COX I and COX II was achieved with the expression of both human COX isoforms in a baculovirus expression system and purification of the enzymes to high levels, as described below in the examples, and also in Barnett, et al., "Purification, Characterization and Selective Inhibition of Human Prostaglandin G/H Synthase 1 and 2 Expressed in the Baculovirus System", *Biochemica Biophysica Acta*, 1209:130–139 (1994). The purified enzymes can readily be obtained in milligram quantities. Furthermore, the recombinant enzymes have the properties of native enzymes and therefore, are suitable for discovery of selective COX II inhibitors.

Accordingly, this invention also pertains to a method Of selecting NSAIDs that will not exhibit adverse GI and renal side effects, comprising the step of testing the drug for its ability to inhibit the enzyme activity of cyclooxygenase I and cyclooxygenase II, wherein selective inhibition of cyclooxygenase II over cyclooxygenase I is indicative of a GI and renal sparing drug. Preferably, this selective inhibition is at least 10-fold, preferably at least 100-fold.

NSAIDs can be tested for inhibition of COX I and COX II activity in any one of several assays that are well known in the art. One such assay is the radiometric assay described in Example 32, which involves the following steps: (1) the enzyme is activated by incubation with phenol and hematin, (2) the sample is combined with the activated enzyme, (3) the mixture is incubated, (4) radiolabeled substrate (arachidonic acid) is added, (5) the mixture in incubated, (6) the reaction is stopped, (7) the product is separated from the substrate, and (8) the product is counted, the level of radioactivity being related to the level of enzyme activity. An enzyme immunoassay can also be used to measure inhibition of COX I and COX II activity. It follows a similar procedure as the radiometric assay, except that the substrate is not radiolabeled and the product ($PGE_2$) is directly measured after the reaction is stopped. Another technique that can be used to measure inhibition of COX I and COX II activity is the oxygen-electrode assay, which follows steps (1) through (4) of the radiometric assay, at which point oxygen consumption is measured.

If the compound is significantly more selective for COX II than for COX I, it will have all the beneficial properties of an NSAID but will not exhibit the adverse effects commonly seen in NSAIDS. It is important to note however, that prodrugs may not be active against purified COX I or COX II in vitro assays such as those described above. First, one must determine what active compound the prodrug is converted to in vivo. Then, the selectivity of the active compound can be measured in an in vitro assay.

Accordingly, the present invention also relates to a method of treating pain and inflammation without obtaining adverse GI and renal side effects, comprising the step of administering to a mammal in need of such treatment a therapeutically effective amount of a compound that selectively inhibits cyclooxygenase II over cyclooxygenase I. As mentioned above, the compounds of the invention are NSAIDs that are GI sparing therapeutic agents. Many of the compounds of the present invention also selectively inhibit COX II over COX I. In particular, Compound (16) has been shown to be significantly more selective for COX II than currently available NSAIDs. Table 2 in Example 32 also lists examples of other compounds of the invention that have shown selectivity for COX II.

Another aspect of the invention relates to the treatment of the above conditions or diseases by the selective inhibition of cyclooxygenase by inhibiting COX II activity.

It is expected that the compounds of the present invention will also have utility as anti-cancer agents. In particular, it is believed these compounds may prevent metastasis of benign and partially transformed colon polyps, as this has been seen in other inhibitors of prostaglandin synthesis. See Moorghen, et al., *Acta Histochemica Suppement-band*39:195–199 (1990).

As mentioned above, the compounds of this invention are administered in a therapeutically effective amount. Administration of the active compounds and salts described herein can be via any of the accepted modes of administration for agents that serve similar utilities.

The level of the drug in a formulation can vary within the full range employed by those skilled in the art. Typically, the formulation will contain, on a weight percent (wt %) basis, from about 0. 01–99. 99 wt % of the drug based on the total formulation, with the balance being one or more suitable pharmaceutical excipients. Preferably, the drug is present at a level of about 1–80 wt %. The actual amount of the compound of Formula (Ia), (Ib), (II) or (III), i. e., the active ingredient, will depend upon numerous factors and will vary with the route and form of administration.

Generally, an acceptable daily dose is about 0.001–150 mg per kilogram body weight of the recipient per day, preferably about 0. 1–75 mg per kilogram body weight per day, and most preferably about 5–20 mg per kilogram body weight per day. Thus, for administration to a 70 kg person, the dosage range would most preferably be about 350 mg to 1.4 g per day. A typical dosage regimen would be, for example, a 500 mg tablet twice daily or a 250 mg tablet taken more frequently.

Administration can be via any accepted systemic or local route, for example, via parenteral, oral (particularly for infant formulations), intravenous, nasal, transdermal or topical routes, in the form of solid, semi-solid or liquid dosage forms, such as for example, tablets, suppositories, pills, capsules, powders, solutions, suspensions, aerosols, emulsions or the like, preferably in unit dosage forms suitable for simple administration of precise dosages. The compositions will include a conventional pharmaceutical excipient and a compound of Formula (Ia), (Ib), (II) or (III) and, in addition, may include other medicinal agents, pharmaceutical agents, carriers, adjuvants, etc. Excipients can be selected from the various oils, including those of petroleum, animal, vegetable or synthetic origin, for example, peanut oil, soybean oil, mineral oil, sesame oil, and the like. Water, saline, aqueous dextrose, and glycols are preferred liquid excipients, particularly for injectable solutions. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. Other suitable pharmaceutical excipients and their formulations are described in "Remington's Pharmaceutical Sciences" by E. W. Martin (Mack Publishing Company, 18th ed., 1990).

If desired, the pharmaceutical composition to be administered may also contain minor amounts of non-toxic auxiliary substances such as wetting or emulsifying agents, pH buffering agents and the like, such as for example, sodium acetate, sorbitan monolaurate, triethanolamine oleate, etc.

The compounds of the present invention can be administered by intravenous injection, for example, by dissolving the compound, salt, ester or ether in a suitable solvent (such as water or saline) or incorporation in a liposomal formulation followed, by dispersal into an acceptable infusion fluid. A typical daily dose of a compound of the invention can be administered by one infusion, or by a series of infusions spaced over periodic intervals.

Oral administration can also be used to deliver the compounds of Formula (Ia), (Ib), (II) and (III) using a convenient daily dosage regimen which can be adjusted according to the degree of affliction. For such administration, a pharmaceutically acceptable, non-toxic composition is formed by the incorporation of any of the normally employed excipients, such as, for example, pharmaceutical grades of mannitol, lactose, starch, magnesium stearate, sodium saccharine, talcum, cellulose, glucose, gelatin, sucrose, magnesium carbonate, and the like. Such compositions take the form of solutions, suspensions, tablets, pills, capsules, powders, sustained release formulations and the like. Such compositions preferably contain about 25–80 wt % of the active ingredient.

Preferably the compositions will take the form of a capsule, pill or tablet and thus the composition will contain, along with the active ingredient, a diluent such as lactose, sucrose, dicalcium phosphate, and the like; a disintegrant such as starch or derivatives thereof; a lubricant such as magnesium stearate and the like; and a binder such as a starch, polyvinylpyrrolidone, gum acacia, gelatin, cellulose and derivatives thereof, and the like. For oral administration to infants, a liquid formulation (such as a syrup or suspension) is preferred.

Pharmaceutical formulations based on liposomes have recently reached human clinical trials. Controlled release liposomal liquid pharmaceutical formulations for injection or oral administration are described in Suzuki, et al., U.S. Pat. No. 4,016,100. Liposomal applications for oral drug delivery of a lyophilized liposome/peptide drug mixture filled into intestine capsules have also been suggested, as in Horikoshi, et al., U.S. Pat. No. 4,348,384. The foregoing are incorporated herein by reference.

For systemic administration via suppository, traditional binders and excipients include, for example, polyalkaline glycol or triglycerides such as PEG 1000 (96%) and PEG 4000 (4%). Such suppositories may be formed from mixtures containing active ingredients in the range of about 1–2 wt %.

Liquid pharmaceutically administrable compositions can, for example, be prepared by dissolving, dispersing, etc. an active compound (about 1–20 wt %), as described above, and optional pharmaceutical adjuvants in a excipient, such as, for example, water, saline, aqueous dextrose, glycerol, ethanol and the like, to thereby form a solution or suspension.

Actual methods of preparing such dosage forms are known, or will be apparent, to those skilled in this art; for example, see "Remington's Pharmaceutical Sciences" supra. The composition to be administered will, in any event, contain a quantity of the active compound(s) in a pharmaceutically effective amount for relief of the particular condition being treated in accordance with the teachings of this invention.

The following preparations and examples are given to enable those skilled in the art to more clearly understand and to practice the present invention. They should not be considered as limiting the scope of the invention, but merely as being illustrative and representative thereof.

| ABBREVIATIONS | |
|---|---|
| DMF | Dimethylformamide |
| DMSO | Dimethylsulfoxide |
| CDI | Carbonyldiimidazole |
| EDTA | Ethylenediaminetetraacetic acid |
| EtOAc | Ethyl acetate |
| Et$_2$O | Diethyl ether |
| FCS | Fetal calf serum |
| HOAc | Acetic acid |
| MeOH | Methanol |
| NaOAc | Sodium acetate |
| THF | Tetrahydrofuran |
| TLC | Thin layer chromatography |

Synthesis Examples

Example 1

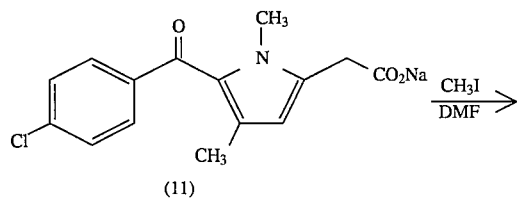

(11)

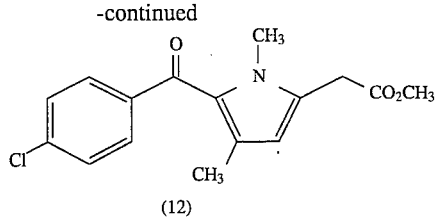

(12)

25 g of the commercially available sodium salt of zomepirac (Sigma), Compound (11), was placed into 150 ml DMF, and 15 ml CH$_3$I was added and stirred at room temperature overnight. TLC indicated a slight amount of starting material. The mixture was then added to 700 ml H$_2$O and extracted with EtOAc (3×). The combined organic layers were washed 5× with H$_2$O and 1× with brine, dried and evaporated to a small volume. An approximately equal volume of hexane (~100 ml of each) was added, the mixture filtered, washed again with hexane, then air dried to yield 20.0 g of the ester, Compound (12).

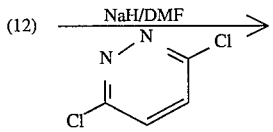

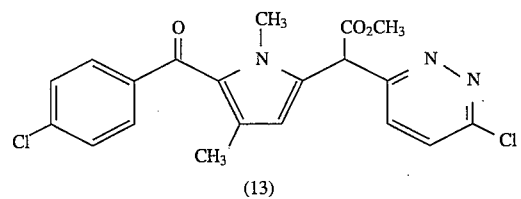

(13)

40 g of Compound (12) was placed into 400 ml DMF, cooled to 0° C. To this mixture was added 45 g of 3,6-dichloropyridazine, and 11.4 g of 60% NaH in 4 portions about 10 minutes apart. When addition was complete, the mixture was removed from the ice bath. Forty-five minutes later, TLC indicated the presence of the starting material ester (no dichloropyridazine). An additional 5 g of 3,6-dichloropyridazine and 750 mg NaH were added and, after ~45 minutes, TLC indicted no ester. The mixture was added to 1400 ml H$_2$O containing 80 g NaHSO$_4$, extracted with EtOAc, washed 5× with H$_2$O, 1× with brine, dried, evaporated, and swirled with a small amount of hexane. The hexane was decanted and discarded. The residue was evaporated to yield Compound (13); m. p137. 5°–138° C.

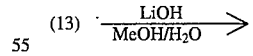

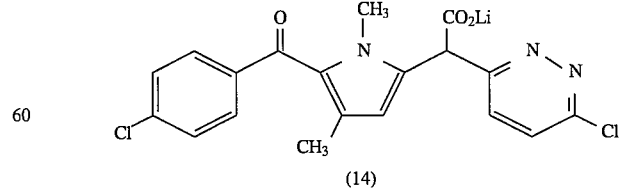

(14)

Compound (13) was placed into 300 ml MeOH. To this mixture was added 100 ml H$_2$O and 11.2 g LiOH. H$_2$O and stirred at room temperature to yield Compound (14).

(14) →[HCl/H₂O]

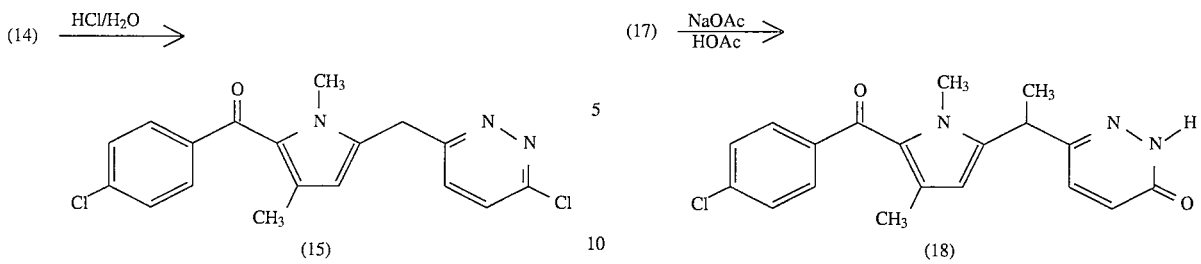

(15)

After ~90 minutes, TLC indicated complete reaction. The mixture was added to a mixture of 1400 ml H₂O and 100 ml concentrated HCl (bubbling noted), and stirred for ~15–20 minutes. The mixture was filtered, the solid washed 2× with H₂O, then stirred with a mixture of 100 ml EtOAc and 200 ml hexane, again filtered, washed with hexane, then air dried to yield 41.2 g of the chloropyridazine compound, Compound (15); m. p157°–159° C.

(15) →[NaOAc/HOAc]

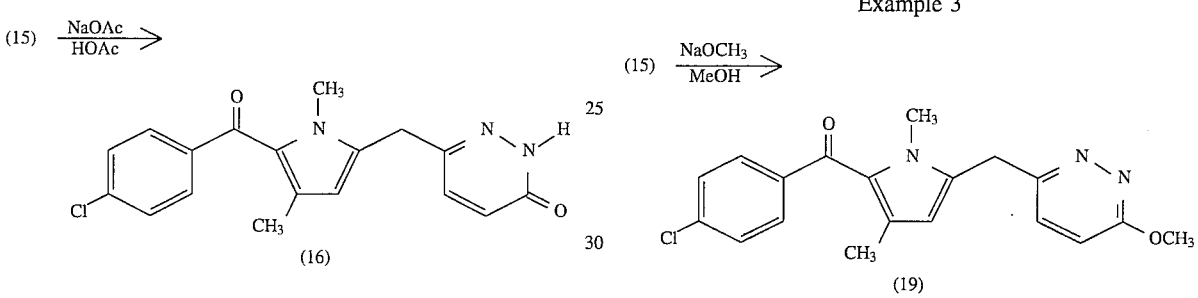

(16)

Compound (15) was placed into 200 ml HOAc, and 10 g NaOAc was added. The mixture was heated at reflux. After ~1 hour TLC showed no starting material. The mixture was removed from heat and added to 1500 ml H₂O. After stirring for ~15 minutes, the mixture was filtered, the solid was stirred with a mixture of ~200 ml acetone/100 ml hexane, filtered again, washed 2× with hexane, and then air dried to yield: 36.0 g of Compound (16); m. p202°–203° C.

Example 2

(15) →[NaH/DMF/CH₃I]

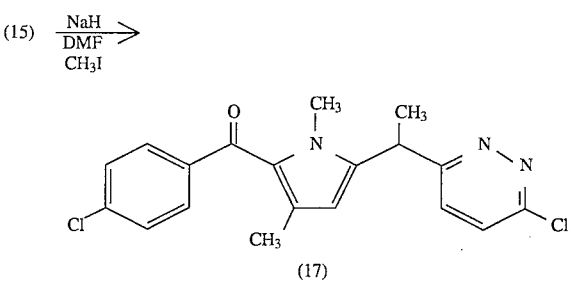

(17)

3. 24 g of Compound (15) from Example 1 was dissolved in DMF, followed by the addition of 430 mg of 60% NaH. The anion was allowed to generate for 30 minutes. To this was added 1. 0 ml of CH₃I. After ~1 hour TLC showed that the reaction was complete. The mixture was added to H₂O, extracted with EtOAc. The organic layer was washed 5× with H₂O and 1× with brine, dried, then evaporated. The mixture was run on a silica gel column in 1:1 EtOAc:hexane (crude product absorbed onto silica gel) to yield 2.3 g of Compound (17).

(17) →[NaOAc/HOAc]

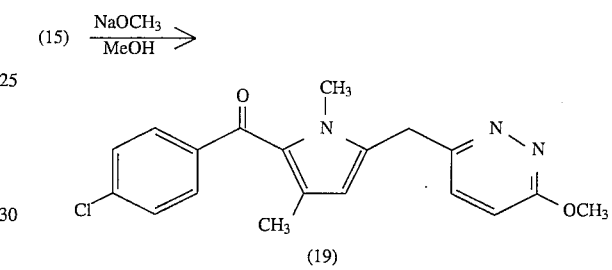

(18)

Compound (17) was placed into 40 ml HOAc and 600 mg NaOAc was added. The mixture was heated at reflux. After ~90 minutes, TLC showed no starting material. The mixture was added to ~300 ml H₂O, stirred at room temperature for ~30 minutes, filtered, washed with H₂O, acetone, and hexane, then dried to yield 1.8 g of Compound (18); m. p194. 1°–196. 0° C.

Example 3

(15) →[NaOCH₃/MeOH]

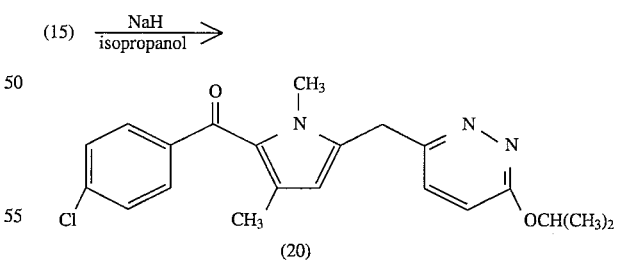

(19)

720 mg of Compound (15) from Example 1 was placed into MeOH (20 ml). To this was added 540 mg NaOCH₃. The mixture was heated to reflux and after ~6 hours, TLC showed no starting material. Dichloromethane was added and the mixture absorbed onto silica gel and evaporated. The silica gel was loaded onto a silica gel column and eluted with 1:1 EtOAc:hexane to yield ~600 mg of product.

The product was stirred with EtOAc and hexane, filtered, and dried to yield 255 mg of Compound (19); m. p. 152. 5°–153. 50° C.

Example 4

(15) →[NaH/isopropanol]

(20)

400 mg of 60% NaH was added to ~20–25 ml of isopropanol. The mixture was stirred at room temperature until all the NaH was consumed. To this gray sandy liquid was added 720 mg of Compound (15) from Example 1. This mixture was heated at reflux. After ~4 hours TLC showed that the reaction was complete. Dichloromethane was added to the mixture to complete dissolution. The mixture was purified as in Example 3, to yield 496 mg of Compound (20); m. p124. 9°–126. 3° C.

Example 5

(15) $\xrightarrow[\text{ethanol}]{\text{Na}}$

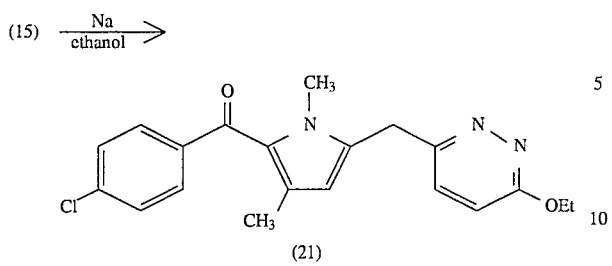

(21)

240 mg of Na was dissolved in EtOH and when all the Na was consumed, 720 mg of Compound (15) from Example 1 was added. The mixture was heated to reflux. After 4 hours, TLC showed no starting material.

The mixture was purified as in Example 3, to yield 421 mg of Compound (21); m. p132. 8°–133. 7° C.

Example 6

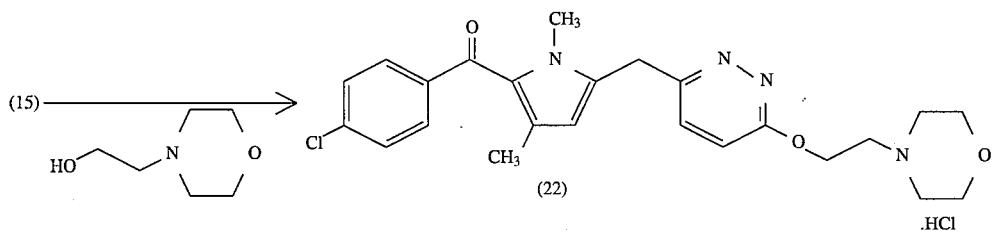

(22)

0.9 ml of morpholino ethanol was dissolved in THF and 400 mg of 60% NaH was added. The Na salt of morpholino ethanol was allowed to form. After all the bubbling had stopped, 720 mg of Compound (15) from Example 1 was added. The mixture was heated at reflux, followed by TLC. After ~3 hours, TLC showed no starting material. Dichloromethane was added, the mixture was absorbed onto silica gel and run on a silica gel column eluting with 95:5 dichloromethane:MeOH. The product from the column was dissolved in EtOAc, then made acidic with an excess of Et$_2$O/HCl and evaporated to give a solid. This was stirred with EtOAc, filtered and dried to yield 446 mg of Compound (22); m. p132. 8°–133. 5° C.

Example 7

(16) $\xrightarrow[\text{DMF}]{\text{Cs}_2\text{CO}_3}$
     $\text{CH}_3\text{I}$

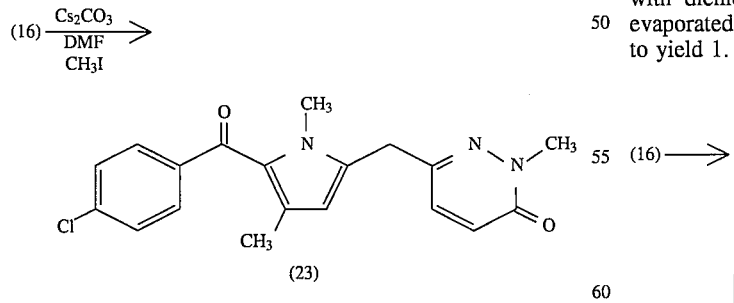

(23)

1.025 g of Compound (16) from Example 1 was dissolved in DMF. To this was added 1.95 g Cs$_2$CO$_3$ (2 equivalents) and 0. 19 ml CH$_3$I and the mixture was stirred at room temperature overnight under nitrogen. TLC indicated virtually complete reaction. The mixture was added to H$_2$O and extracted with EtOAC. The organic layer was washed 5× with H$_2$O and 1× with brine, dried and evaporated. This was purified on a silica gel column, eluting with 5% dichloromethane:MeOH to yield ~300 mg of Compound (23). This was recrystallized from acetone:hexane to yield 249 mg of Compound (23); m. p139. 9°–140. 2° C.

Example 8

(16) ⎯⎯→

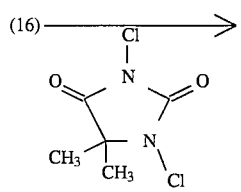

-continued

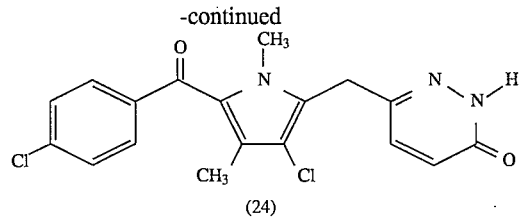

(24)

2.72 g of Compound (16) from Example 1 was placed into a mixture of 240 ml of 1:1 THF:acetone. To this mixture, at ice bath temperature, was added 1.68 g of 1,3-dichloro-5, 5-dimethylhydantoin. The mixture was stirred at 0° C. and followed by TLC, until the reaction was complete. The mixture was added to ~500 ml of 5% Na$_2$SO$_3$, extracted with dichloromethane, washed 1× with H$_2$O, dried and evaporated. The residue was stirred with EtOAc and filtered to yield 1. 5 g of Compound (24); m. p247. 2°–248. 5° C.

Example 9

(16) ⎯⎯→

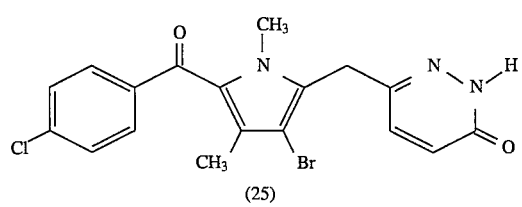

(25)

1.36 g of Compound (16) was placed into 120 ml 1:1 THF:acetone. This mixture was cooled to 0° C. and 1.23 g of 1,3-dibromo-5,5-dimethylhydantoin was added. The mixture was stirred at ice bath temperature for ~60 minutes. The mixture was added to a solution of 5% NaSO₃, extracted with dichloromethane, washed 2× with H₂O and 1× with brine, dried, and evaporated. The crude product was stirred with EtOAc, filtered, and dried to yield 1.33 g of Compound (25); m. p231. 0°–231. 5° C.

Example 10

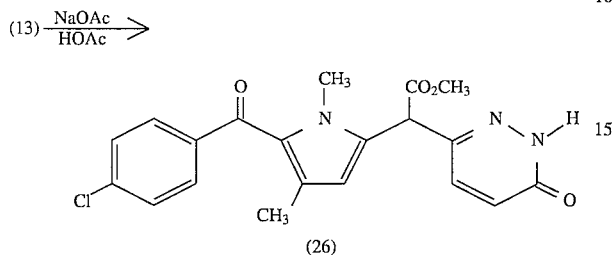

4.0 g of Compound (13) from Example 1 was placed into 35 ml HOAc with 1.5 g NaOAc and heated at reflux. After ~90 minutes, TLC showed no starting material. The reaction was added to H₂O, the mixture filtered, and the solid was stirred with EtOAc/hexane, filtered, and dried to yield 3. 5 g of Compound (26); m. p216°–217. 5° C.

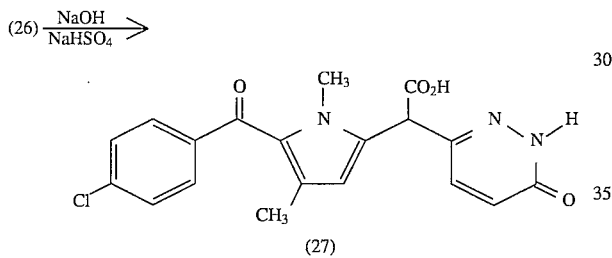

1.59 g. of Compound (26) was placed into 20 ml of MeOH. 12 ml of 0.98M NaOH was added and the mixture was stirred at room temperature. After 2 hours TLC showed no starting material. The mixture was added to a solution of NaHSO₄ (5 g/300 ml), cooled, stirred for 20 minutes and filtered. The product was washed with hexane, stirred with acetone/hexane, and dried to yield 1.14 g of Compound (27). This compound was characterized as it sodium salt, Compound (28).

Example 11

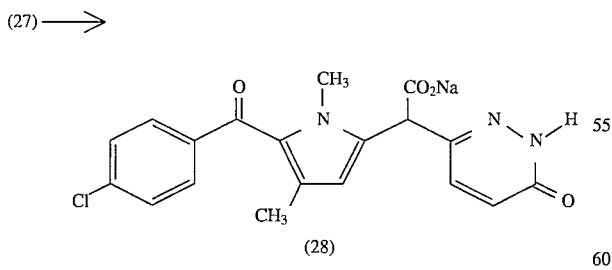

385 mg of Compound (27) from Example 10 was placed into MeOH. To this was added 84 mg of NaHCO₃ dissolved in the minimum amount of water. The mixture was stirred at room temperature for 10 minutes and evaporated to dryness to yield 355 mg of Compound (28); m. p189°° C. (effervesces).

Example 12

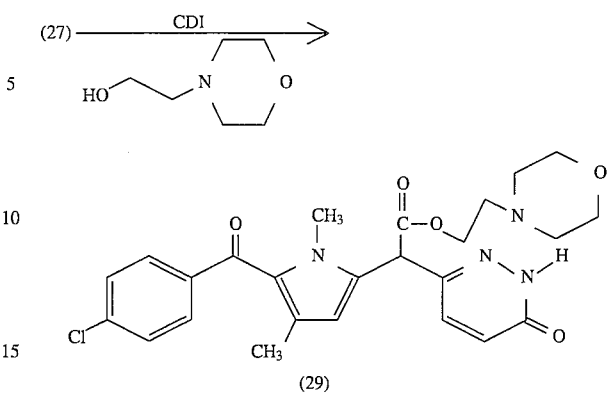

385 mg of Compound (27) from Example 10 was placed into THF. To this was added 200 ml of CDI and 0. 15 ml of morpholino ethanol. This mixture was stirred at room temperature overnight. TLC showed a mixture of Compound (29) and decarboxylated material, Compound (16). The mixture was added to H₂O, extracted with EtOAc, washed 1× with brine and 1× with H₂O, dried and evaporated. This was run on a silica gel column in 95:5 dichloromethane:MeOH. The product was dissolved in EtOAc, the solution was acidified with HCl Et20, then evaporated to dryness. The residue was stirred with EtOAc, filtered and dried to yield 167 mg of Compound (29); m. p162. 5° C. (effervesces).

Example 13

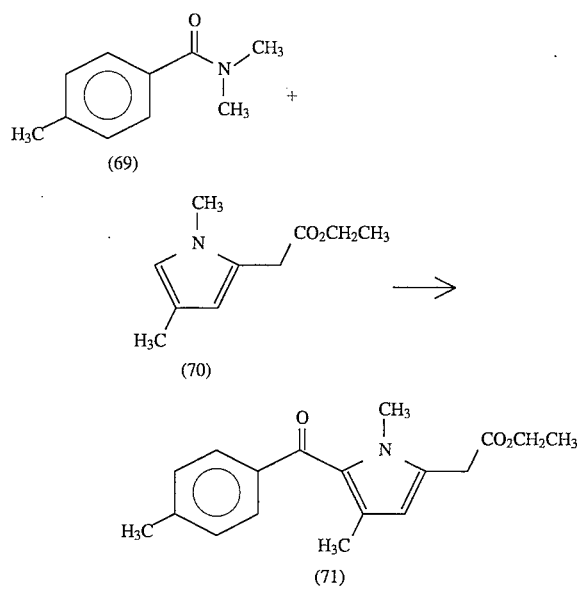

A solution of Compound (69) (7.6 g0. 05 mole) and POCl₃ (7.46 g, 0. 048 mole) in dichloroethane (100 ml) was refluxed for 45 minutes, then cooled to room temperature and Compound (70) (5.0 g, 0. 025 mole) in dichloroethane (20 ml) was added. The reaction was refluxed for 4 hours and then stirred at room temperature for 18 hours. A solution of NaOAc (4.5 g, 0. 54 mole) in 200 ml of H₂O was added and the mixture refluxed for 2 hours. The two phases were separated, the aqueous extracted with dichloromethane (2×100 ml), the organics combined and dried over Na₂SO₄, and concentrated. The crude material was purified by column with FLORISIL® using 9:1 hexane:EtOAc to give 5.1 g (67% yield) of Compound (71).

Example 14

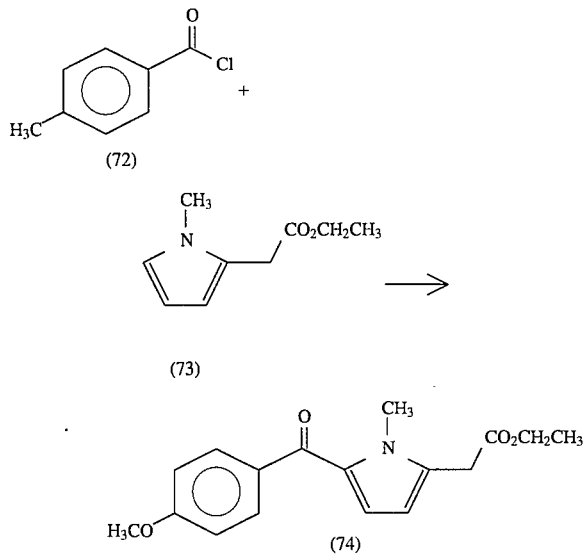

A solution of Compound (73) (2.0 g, 0. 012 mole) and Compound (72) (6.12 g, 0. 036 mole) in 50 ml of xylene was refluxed for 60 hours. The solution was poured on a column of alumina and eluted with hexane followed by 9:1 hexane:EtOAc to give 2.0 g (56% yield) of Compound (74).

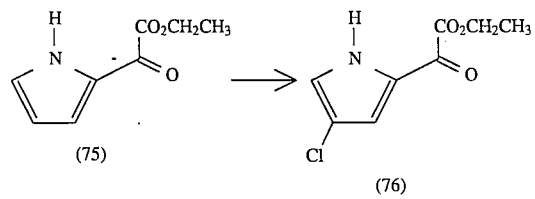

Compound (75) was synthesized by the procedure described in Behr, et al., *Acta Chem. Scan*27:2411 (1973). A solution of Compound (75) (50 g, 0. 29 mole) in 500 ml of acetone was cooled to 5° C with mechanical stirring1,3-dichloro-5,5-dimethylhydantoin (65.0 g, 0. 32 mole) was added and the reaction allowed to reach 15° C. The reaction was stirred for 1 hour and poured into 1 liter of 10% NaHSO$_3$, extracted with EtOAc (3×300 ml), the organics combined and washed with H$_2$O (500 ml), dried over Na$_2$SO$_4$ (anhydrous) and concentrated. The crude material was purified by column on silica gel using 95:5 hexane:EtOAc to obtain 25 g (42% yield) of Compound (76).

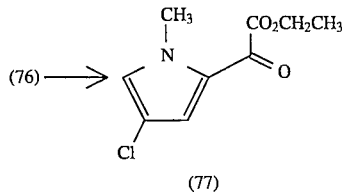

To a solution of Compound (76) (10.0 g, 0. 049 mole) in DMF (25 ml) was added K$_2$CO$_3$ (anhydrous) (8.25 g, 0. 059 mole) at room temperature. After stirring for 1 hour, the suspension was cooled to 5° C, methyl iodide added (3. 3 ml, 0. 054 mole) and stirring continued for 3 hours. The reaction was poured into a cooled solution of 10% HCl (500 ml), extracted with EtOAc (3×500) and the organics washed with H$_2$O (5×100 ml), dried over NA$_2$SO$_4$ (anhydrous) and concentrated to give 14.0 g of crude product. This was purified on FLORISIL using 9:1 hexane:EtOAc to obtain 11.5 g (100% yield) of Compound (77).

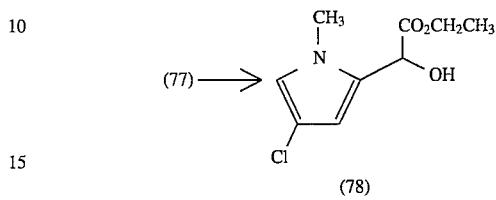

To a suspension of NaBH$_4$ (14.8 g, 0. 39 mole) in 100 ml of ethanol and 20 ml of H$_2$O at −78° C. was added Compound (77) (28.0 g, 0. 13 mole) in 500 ml of methanol. The reaction was allowed to reach −50° C. and was stirred with a mechanical stirrer for 2 hours. Then the reaction was brought to pH=8 with HOAc:H$_2$O, concentrated, and the residue dissolved in EtOAc (300 ml). The organic phase was washed with H$_2$O, dried over Na$_2$SO$_4$ and concentrated to give Compound (78) as a white solid (26 g) that was used without purification in the next reaction.

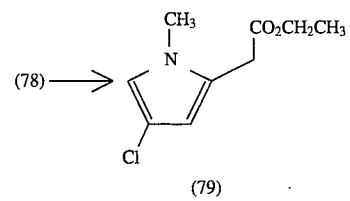

To a solution of iodine (28.0 g, 0. 11 mole) in 1 liter of benzene with mechanical stirring, was added PPh$_3$ (59.0 g, 0. 22 mmole). After 10 minutes, a yellow solid was formed. The crude Compound (78) (26.0 g) was added as a solid and the reaction stirred for 3 hours at room temperature. The reaction was filtered through CELITE® and the volume was reduced to on third and this was applied to a column of FLORISIL and eluted with 9:1 hexane:EtOAc to obtain 14.0 g (54% yield, two steps) of Compound (79).

Example 16

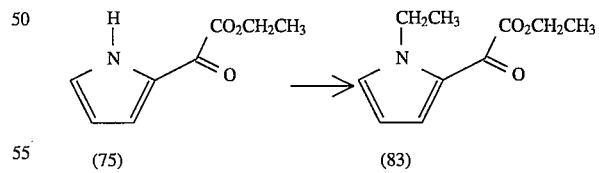

To a suspension of NaH/mineral oil 50% (10.8 g, 0. 23 mole) in 20 ml of DMF, cooled in an ice bath, was added Compound (75) (See example 15) (25.0 g, 0. 15 mole) in 50 ml of DMF. It was allowed to react for 2 hours at room temperature, then cooled in an ice bath and treated with ethyl iodide (23. 99 ml, 0. 3 mole). The reaction was stirred for 4 hours at room temperature then poured into a 10% HCl solution, cooled and the aqueous extracted with ethyl acetate (2×300 ml), and the combined organic phases washed with H$_2$O (5×300 ml), dried over Na$_2$SO$_4$ and concentrated. The crude material was purified on a column of FLORISIL eluted with 9:1 hexane:EtOAc to obtain 8.6 g (30% yield) of Compound (83).

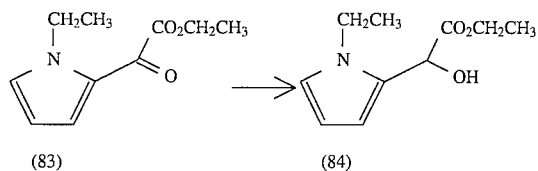

A solution of Compound (83) (8.6 g, 0. 044 mole) in 300 ml of MeOH was cooled to −70° C. and NaBH₄ (5.0 g, 0. 13 mole) was added. The reaction was stirred for 3 hours at −70° C., then neutralized to pH=8 with 1:1 HOAc:H₂O. The solvent was almost evaporated, and the residue dissolved in 300 ml of EtOAc, washed with H₂O (200 ml), dried over NA₂SO₄ and concentrated to give 9.0 g of Compound (84) as a white solid that was used in the next reaction.

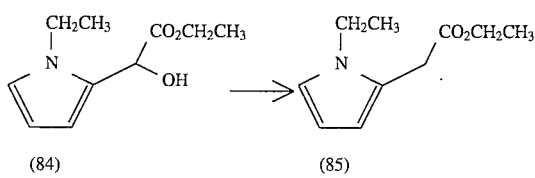

Compound (84) (9.0 g 9) was dissolved in 1,2-dichloroethane (50 ml). ZnI₂ (21.92 g, 0.07 mole) was added, followed by NaBH₃CN (14.35 g, 0.23 mole) at room temperature. The reaction was stirred for 5 hours at room temperature then poured into ice water. The compound was extracted with EtOAc (250 ml), the organic phase washed with H₂O, dried over Na₂SO₄ and concentrated to obtain 7.2 g of crude product. This was purified on a column using FLORISIL and eluting with 9:1 hexane:EtOAc to obtain 2.0 g (24% yield, two steps) of Compound (85).

Example 17

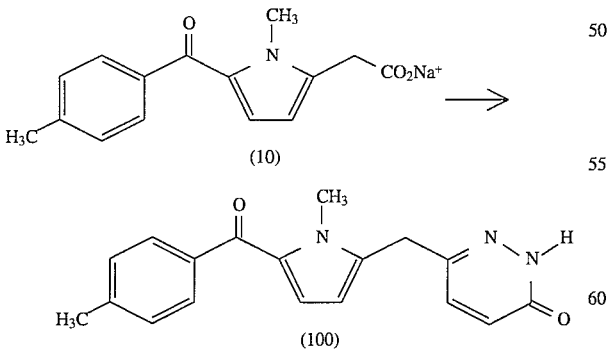

Compound (100) was synthesized as described in Example 1, using the commercially available sodium salt of tolmetin (Sigma), Compound (10), as the starting material.

Example 18

(100) ⟶

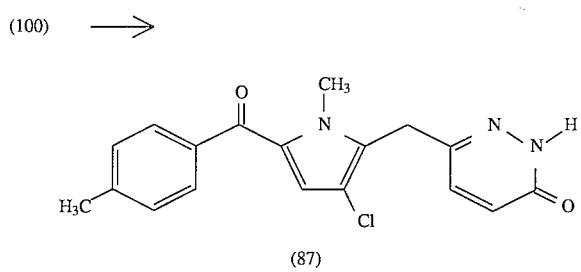

To a solution of Compound (100) from Example 17 (300 mg, 0.97 mmole) in 15 ml of acetone and 15 ml of THF at 5° C., was added 1,3-dichloro-5,5-dimethylhydantoin (192 mg, 0.97 mmole). The reaction was allowed to reach room temperature and after 1 hour, a additional 30 mg of 1,3-dichloro-5,5-dimethylhydantoin was added. After 10 minutes, the reaction was poured into a 5% NaHSO₃ solution and extracted with EtOAc (2×50 ml). The organic phase was washed with H₂O and brine, dried over Na₂SO₄ and concentrated. The crude material was purified on preparative TLC. (EtOAc) to obtain 161 mg (48% yield) of Compound (87); m.p212°–214° C.

Example 19

(100) ⟶

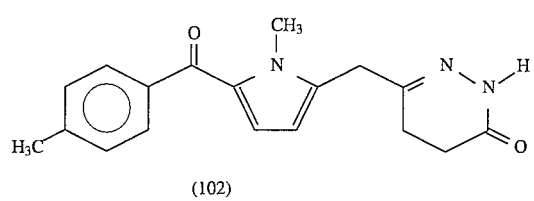

A suspension of Compound (100) from Example 17 (1.5 g, 4.9 mmole) and activated Zn (0.96 g, 14.6 mmole) in 25 ml of HOAc was refluxed for 3 hours with vigorous stirring. The reaction was filtered through CELITE and the residue washed with dichloromethane. The solution was evaporated and the solid (1.55 g) crystallized (EtOAc) to give 774 mg (51% yield) of Compound (102) as crystals; m.p171°–172° C.

Example 20

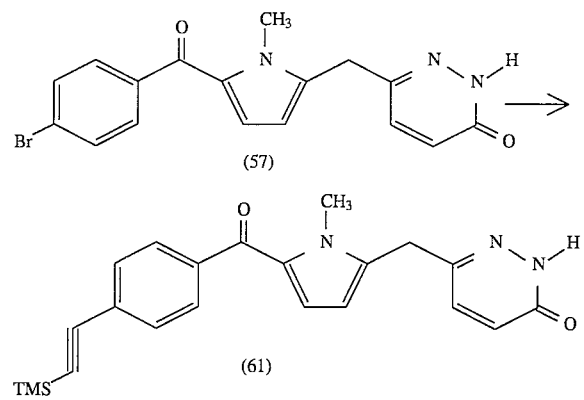

Compound (57) was synthesized according to the method described in Scheme A, Steps 1–4a.

A solution of Compound (57) (0.4 g, 0.011 mole), trimethylsilylacetylene (excess), palladium diacetate (24 mg, 0.1 mmole) and PPh$_3$ (47 mg, 0.18 mmole) in triethylamine (6 ml) and acetonitrile (3 ml) was refluxed for 4 hours under argon. The reaction was concentrated and the crude purified on flash chromatography (EtOAc) to give Compound (61) (380 mg, 90% yield).

(61) ⎯⎯→

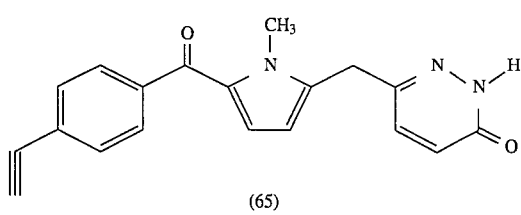

(65)

A suspension of Compound (61) (365 mg, 0.94 mmole) and K$_2$CO$_3$ (30 mg) in methanol (10 ml) was stirred for 2.5 hours at room temperature. The solvent was removed and the residue purified by flash chromatography (silica gel) using EtOAc to obtain Compound (65) (184 mg, 62% yield); m.p185°–187° C. (hexane:acetone).

Example 21

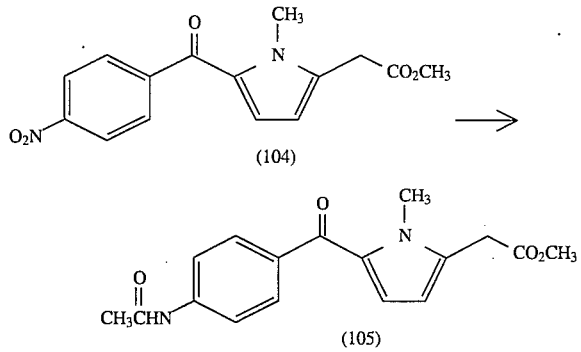

Compound (104) was synthesized according to the method described in Scheme A, Step 1.

A solution of Compound (104) (2.5 g, 8.3 mmole), Ni$_2$B (2.5 g) and 1M HCl (35 ml) in methanol (140 ml) was placed in an oil bath at 65° C. for 30 minutes. The reaction was brought to basic pH with concentrated NH$_{41}$H, extracted with EtOAc and the organic extracts dried over Na$_2$SO$_4$ and evaporated. The crude extract was purified by column (6:4 hexane:EtOAc) to obtain the desired aniline product (2.03 g, 90% yield).

The aniline product (2.2 g, 8.1 mmole) and acetic anhydride (25 ml) in pyridine (50 ml) was stirred at room temperature for 18 hours. The reaction was concentrated and azeotroped with toluene to give the crude Compound (105) as a white solid (2.35 g) which was used in subsequent reactions without purification.

Example 22

(15) ⎯⎯→

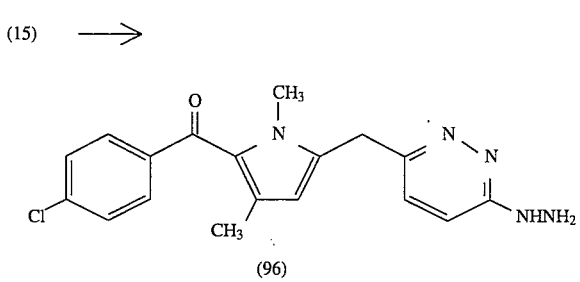

(96)

5.0 g of Compound (15) from Example 1 was suspended in 14 ml anhydrous hydrazine and 2 ml of n-butanol. The reaction was heated to reflux, at which time the solid dissolved and the reaction was homogeneous. After 1 hour of reflux TLC. (20% ethyl acetate/hexane) indicated that all of the starting material had been consumed. The reaction was cooled to room temperature, at which time a precipitate formed. The reaction was filtered, the solid washed 2× with water, 2× with ether and placed under vacuum (approximately 0.1 mm Hg) for 3 hours to give 5.45 grams (>100%)2.0 g of this solid was recrystallized from water/DMSO to give 1.45 g of Compound (96). The rest of the material was used as obtained in further reactions.

(96) ⎯⎯→

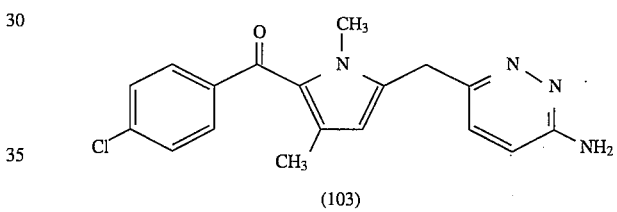

(103)

300 mg of Compound (96) was suspended in 20 ml absolute methanol, and approximately 500 mg Raney Nickel (washed 3× with methanol) was added as a suspension in methanol (3×2 ml). The mixture was heated at reflux for 2 hours. The reaction was cooled, filtered through a glass filter pad and rotovaped to give a yellow solid. Recrystallization (CH$_3$CN/DMF/water) gave 215 mg of Compound (103); m.p206.8°–209° C. Theoretical: C, 63.44; H, 5.03; N, 16.44. Found: C, 63.26; H, 4.98; N, 16.53.

Example 23

(15) ⎯⎯→

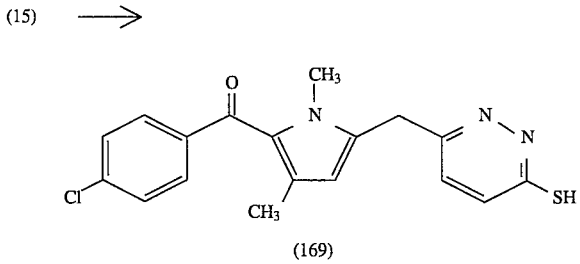

(169)

500 mg of Compound (15) from Example 1 was dissolved in 3 ml absolute ethanol127 mg of thiourea (1.2 eq., 1.67 mmol) was suspended in this mixture, and the reaction was heated to reflux. The solution became homogeneous at reflux, followed by formation of a precipitate after about 15 minutes. The reaction was heated for a total of 45 minutes. TLC. (20% ethyl acetate/hexane) showed no change, however the precipitate had stopped forming at this point. The reaction was cooled and the ethanol removed in vacuo. To this solid was added a solution of 147 mg sodium carbonate (1 eq., 1.39 mmol) dissolved in 1 ml water. The reaction was stirred for 15 minutes, filtered, the solid residue obtained was then washed with water and ethanol. Recrystallization (acetone/hexane) gave 275 mg of an olive green solid, Compound (169); m.p220.4°–222.4° C. Theoretical: C, 60.41; H, 4.51; N, 11.74. Found: C, 60.15; H, 4.34; N, 11.80.

Example 24

As mentioned above, Compound (16) has been found to exist in at least three crystal forms (Phase I, Phase II and Phase III) and two hydrates (Hydrate I and Hydrate II).

Phase I was obtained when Compound (16) was recrystallized from methanol, ethanol, ethanol/acetic acid, acetone, ethyl acetate, ethyl acetate/acetic acid, dichloromethane, tetrahydrofuran or tetrahydrofuran/ethyl acetate. Unmilled Phase I (–200 μm) was found to be physically stable at 40° C./75% relative humidity for at least 4 days. Milling and micronization did not cause any phase transformation. When suspended in water, Phase I converted to a monohydrate, Hydrate I. Hydrate I can be converted back to Phase I by suspension in alcohol.

Phase II was obtained when Compound (16) was recrystallized from toluene. When suspended in water, Phase II was converted to another hydrate, Hydrate II. When suspended in alcohol or ethyl acetate, Phase II converted to Phase I.

Phase III was obtained by rapid precipitation of Compound (16) from acetic acid/water. When suspended in water, Phase III converted to Hydrate I. When suspended in alcohol, Phase III converted to Phase I.

Hydrate I, a monohydrate, was also obtained by slow recrystallization of Compound (16) from acetic acid/water. Hydrate I was found to be physically stable at 40° C./ambient relative humidity, within the range of 11–95% relative humidity, and 40° C./75% relative humidity (14 days). Dehydration at temperatures below 100° C. produced a metastable form that converted back to Hydrate I at ambient conditions and 23% relative humidity. Heating Hydrate I at 120° C. caused a phase conversion to another anhydrous crystal form.

Based upon their characteristics and physical properties, both Phase I and Hydrate I were selected for further evaluation in bioavailability and formulation studies.

Formulation Examples

The following examples illustrate the preparation of representative pharmaceutical formulations containing Compound (16) as the active ingredient. Other compounds of Formula (Ia), (Ib), (II) and (III), such as those prepared in accordance with Examples 1–23, can be used as the active ingredient in preparation of the formulations of these examples.

Example 25

This example illustrates the preparation of a representative pharmaceutical formulation for oral administration containing Compound (16). Compound (16) and povidone were combined in a weight ratio within the range of 1:0.5 to 1:5 to form a solid dispersion. Compound (16) and povidone were first dissolved in HOAc at 80° C. then evaporated quickly at 110° C, under vacuum. The remaining material was then introduced into a hard-shell gelatin capsule or Syntex Suspension Vehicle ("SSV"; 0.9% NaCl, 0.5% sodium carboxymethylcellulose, 0.4% polysorbate 80, 0.9% benzyl alcohol and 97.3% distilled water).

The process used in this example, along with that described in Example 26 creates a homogeneous material made up of relatively small crystals and/or amorphic state of drug uniformly dispersed through out a soluble matrix. Dissolution studies in water showed that this matrix promotes rapid initial release of the drug.

Compound (16) and povidone can also be dissolved in other solvents such as ethanol, methylene chloride and ethanol:methylene chloride.

Example 26

This example illustrates the preparation of another representative pharmaceutical formulation for oral administration, containing Compound (16). Compound (16) and citric acid were combined in a weight ratio within the range of 1:1.2 to 1:1.5 to form a solid dispersion. Compound (16) was melted in citric acid at 165° C. to dissolve the drug, then chilled on an ice bath. The remaining material was then introduced into a hard-shell gelatin capsule or SSV.

Example 27

This example illustrates the preparation of another representative pharmaceutical formulation for oral administration containing the active compound, Compound (16), where:

| Ingredient | Quantity per tablet, mg |
| --- | --- |
| active compound | 400 |
| cornstarch | 50 |
| croscarmellose sodium | 25 |
| lactose | 120 |
| magnesium stearate | 5 |

The above ingredients are mixed intimately and pressed into single scored tablets.

Example 28

This example illustrates the preparation of another representative pharmaceutical formulation containing the active compound, Compound (16). A suspension for oral administration is prepared having the following composition:

| Ingredient | Amount |
| --- | --- |
| active compound | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml | where "q.s." means adding a quantity sufficient to achieve a stated function, e.g., to bring a solution to a desired volume such as 100 ml.

Example 29

This example illustrates the preparation of a representative injectable pharmaceutical formulation containing the active compound, Compound (16). The injectable preparation, buffered to a suitable pH, is prepared having the following composition:

| Ingredient | Amount |
| --- | --- |
| active compound | 0.2 g |
| sodium acetate buffer solution, 0.4M | 2.0 ml |
| Cl (1N) or NaOH (1N) | q.s. to suitable pH |
| water (distilled, sterile) | q.s. to 20 ml |

Example 30

This example illustrates the preparation of a representative pharmaceutical formulation for topical application containing the active compound, Compound (16), where:

| Ingredient | Amount, g |
| --- | --- |
| active compound | 0.2–10 |
| Span 60 | 2 |
| TWEEN ® 60 | 2 |
| mineral oil | 5 |
| petrolatum | 10 |
| methyl paraben | 0.15 |
| propyl paraben | 0.05 |
| BHA (butylated hydroxy anisole) | 0.01 |
| water | q.s. to 100 |

All of the above ingredients, except water, are combined and heated to 60–70° C. with stirring. A sufficient quantity of water at 60° C. is then added with vigorous stirring to emulsify the ingredients, and water then added q.s100 g.

Example 31

This example illustrates the preparation of a representative suppository pharmaceutical formulation containing the active compound, Compound (16). A suppository totalling 2.5 grams is prepared with witepsol (triglycerides of saturated vegetable fatty acid; Riches-Nelson, Inc., New York) and has the following composition:

| active compound | 500 mg |
| --- | --- |
| witepsol H-15 | balance |

Testing Examples

The anti-inflammatory and analgesic activity of the compounds of the invention can be determined by a variety of assays utilizing both in vitro and in vivo procedures, such as by following, for example, the procedures described in the examples below, or modifications thereof. In this manner, the potency and selectivity of compounds useful as NSAIDs can be determined.

Materials

Human prostaglandin G/H synthase I and II ("COX I" and "COX II") were expressed in the baculovirus expression system and purified to high levels. Both enzymes were glycosylated and possessed both cyclooxygenase and peroxidase activities.

Transplacement plasmid construction

A 2 Kb fragment containing the coding region of COX I (Oxford Biomedical Research, Inc. Oxford, Mich.) was cloned into the plasmid pBS (Stratagene, La Jolla, Calif.). The fragment was released from the resulting plasmid, pBS/COX $I_{hum}$, by digesting with XhoI and SspI and then isolated by agarose gel electrophoresis. The resulting fragment contained, in addition to the coding sequence for COX I, the 5' flanking sequence, CTCGATG, and 160 bp of the 3' noncoding sequence. The fragment was purified using Elu-Quik (Schleicher & Schuell, Inc., Keene, N. H.) following the manufacturer's protocol, then ligated into the XhoI-SmaI sites of pSyn XIV $VI^+X3$, Wang, et al., Gene 100:131–137 (1991). The resulting transfer vector was designated "pCOX I".

A 1.8 Kb DNA fragment containing the coding region of human COX II was generated by PCR using pcDNA/COX II (Hla, et al., Proc. Natl. Acad. Sci. USA 89:7384–7388 (1992)) as the template, GAATTCTAAATATG CTCGC-CCGCGCCCTGCTG as the 5' primer and ATTAGACTTC-TACAGTTCAGTCGAAC as 3' primer. These primers were designed to amplify the coding sequence for COX II with TAAAT, a sequence that gives optimal translation of very late baculovirus genes (Matsuura, et al., J. Gen. Virol 68:1233–1250 (1987)), juxtaposed to the initiation codon of the COX II gene. The template was denatured at 94° C. for 1 minute, the primers allowed to anneal at 55° C. for 2 minutes and the extension reaction was at 72° C. for 3 minutes. Thirty cycles of amplification were completed. The resulting 1.8 Kb DNA fragment was digested with EcoRI and Bgl II and cloned into EcoRI/Bgl II digested pSyn XIV $VI^+X3$. Several clones were sequenced and one that contained the correct sequence was selected and designated "pCOX II".

Generation of recombinant virus

A DNA solution consisting of 0.5 µg baculovirus virion DNA (Baculogold®, PharMingen, San Diego, Calif.) and 5 µg transplacement plasmid DNA (COX I or COX II) in HBS (20 mM Hepes, 150 mM NaCl, pH 7.4) was prepared. Immediately prior to transfecting Sf9 baculovirus cells, 1.5 ml of the DNA solution was mixed with an equal volume of lipofectin (0.67 µg lipofectin/ml HBS), Felgner, et al., (1987) Proc. Natl. Acad. Sci 84:7413–7417 (1987). Sf9 cells in Ex-Cell 400 media (JRH Scientific, Woodland, Calif.) were seeded into T-25 flasks ($3 \times 10^6$ cells/flask). After approximately 1 hour, when the cells had attached to the flask, the medium was decanted and the cell monolayer washed with HBS3 ml of the lipofectin-DNA mixture was then layered over the cells. After 40 minutes at 28° C., 3 ml of Ex-Cell 400 supplemented with 10% FCS and gentamicin (50 µg/ml) were added to the flask to dilute the lipofectin-DNA solution. After 30 minutes the lipofectin-DNA solution was replaced with fresh Ex-Cell 400 (with 2.5% heat inactivated FCS). Five days later the supernatant was collected and clarified by centrifugation (800×g, 15 min). Ten-fold serial dilutions of the clarified supernatant in Ex-Cell 400 were then prepared. Sf9 cells were seeded in 6 well plates at a density of $0.8 \times 10^6$ cells/well. When the cells attached, the medium was decanted and 0.5 ml of the serially diluted culture fluid from transfected cells was gently pipetted onto the monolayers. The cells were incubated at room temperature with gentle agitation every 15 minutes. After 1 hour, the virus inocula were aspirated and the cells overlayed with 2 ml Ex-Cell 400 containing 1.5% melted agarose. Five days later an additional 2 ml Ex-Cell 400-agarose containing 3% neutral red was layered over the first agarose overlay. The next day, unstained plaques were counted to determine the virus titer. Well separated plaques were picked and aspirated into 1 ml medium which was then inoculated onto Sf9 monolayers in 6 well plates. Three days later, when most cells contained polyhedra, the cells were harvested and assayed for COX activity. Virus in the culture fluid from cells expressing either COX I or COX II were designated vCOX I and vCOX II respectively and used as virus seed for production of the enzymes.

Production of COX I and COX II

In order to produce high levels of COX I and COX II, 9.5 liters of Sf9 cells growing exponentially in bioreactors were infected with either vCOX I or vCOX II at a multiplicity of infection of 0.5 plaque forming units per cell. At the time of infection, the cultures were fed 400 ml of a nutrient solution consisting of glucose, glutamine, yeastolate, and lipids, Nguyen, et al., *J. Biotechnol.* 31:205–217 (1993). The cells were harvested by centrifugation three days later. The pellets were stored frozen at −80° C. until needed for purification of COX I and COX II.

Purification of COX I

Pellets of cells infected with vCOX I were thawed in chilled, deoxygenated lysis buffer (5 mM Tris, pH 8, containing 1 µg/ml pepstatin, 1 µg/ml leupeptin, 1 mM pefabloc SC. (Pentapharm AG, Basel, Switzerland) and 10% glycerol)5 ml of buffer was utilized for each $1\times10^8$ cells lysed. The cells were disrupted. Centrifugation at 800×g for 10 minutes pelleted nuclei and other debris which were extracted once again in half the original lysis buffer. Microsomes from the 800×g supernatant were pelleted by centrifugation (105,000×g, 1 hour). The pellet was suspended in solubilization buffer (5 mM Tris, pH 8, containing 1 µg/ml pepstatin, 1 µg/ml leupeptin, 1 mM pefabloc SC) by sonication5 ml of buffer was utilized for each $2\times10^8$ cells lysed. One volume of 2% (w/v) TWEEN® (polyoxyethylenesorbitan monolaurate, Atlas Chemie G. m. b. H.) in solubilization buffer was added to each volume of suspended microsomes which were solubilized by gently rocking at 4° C. for 1.5 hours. Insoluble debris was then removed by centrifugation (105,000×g, 1 hour). The solubilized COX I Was filtered through a 0.45 µm pore size filter and diluted with 1 volume of buffer used to equilibrate the ion-exchange column. An anion-exchange HPLC column (Bio-Gel, DEAE, 5-PW, 150×21.5 mm, BioRad Inc., Richmond Calif.) was equilibrated against mobile phase A (5 mM Tris, pH 8, 0.1% TWEEN 20, 10% glycerol). Solubilized COX I from $8\times10^8$ cells was loaded onto the column which was then washed with mobile phase A until the UV absorbance (at 280 nm) returned to baseline (8 ml/min flow rate). Retained proteins were then eluted with a linear NaCl gradient to 0.4M over a 40 min interval. The salt concentration was then increased to 1M in 10 additional minutes. Fractions containing enzyme activity (radiometric assay method) were pooled and diluted with 3 volumes of Tris buffer (20 mM Tris, pH 7.5 containing 0.5M NaCl) for further purification. A column packed with lentil lectin sepharose 4B (Pharmacia, Piscataway, N.J.) was equilibrated against Buffer A (20 mM Tris pH 7.5, 0.5M NaCl, 0.02% TWEEN 20). Typically a 2.5 cm diameter column was packed to a bed height of 4.5 cm (0.8 ml/min flow rate). Pooled fractions from the ion-exchange column containing COX I were then loaded onto the column which was washed with Buffer A until the UV adsorption at 280 nm returned to baseline. The retained proteins were then eluted with an 18 minute gradient against Buffer B (buffer A+0.5M alpha-methylglucoside). The column was washed for 62 more minutes until all proteins had eluted. Fractions were assayed for enzymatic activity and the fractions containing COX I were pooled for further processing. The COX I from the lectin column was concentrated approximately 8 fold using a Centriprep 30 (Amicon, Danvers, Mass.). Up to 0.5 ml of the concentrated sample was injected into a gel filtration column (SPDx75, HR 10/30, 1×30 cm). The mobile phase was 50 mM Tris pH 7.5, 0.1% TWEEN 20 (0.5 ml/min flow rate). COX I was found in the excluded volume at 11 minutes, while smaller molecular weight contaminants were washed through the column in 29 minutes. The purified enzyme was stored frozen at −80° C. until needed.

Purification of COX II

COX II was extracted from pellets of cells infected with vCOX II and purified in a manner similar to COX I with a few exceptions: (1) diethyldithiocarbamate (100 µM) was added for the disruption buffer, but glycerol was omitted; (2) dodecylmaltoside (2.5%) was substituted for TWEEN 20 in the solubilization buffer; (3) the 0–40% B ion-exchange gradient was reduced to 20 minutes; (4) the ion-exchange pool was not diluted prior to loading on the lectin column; (5) the loading mobile phase of the lectin column was 20 mM Tris —HCl pH 8.0, 0.2M NaCl, 0.1% octylglucoside; and (6) the mobile phase of the gel-filtration step was 50 mM Tris pH 8 plus 0.1% octylglucoside and the flow rate was 0.75 ml/min.

Example 32

Enzymology: Activities Against COX I and COX II

As described above, human recombinant COX I and COX II were cloned and expressed in a baculovirus system. Partially purified COX I and COX II enzymes were used for screening compounds for their ability to inhibit COX I and COX II activity, as described below.

Compound (16), in 2 µl DMSO, and control samples (carrier vehicles only) were mixed with COX I or COX II samples (e.g. fractions from the chromatography columns) in polypropylene tubes and preincubated with 2 mM phenol for 5 minutes and then with 1 µM hematin for an additional 5 minutes. The 150 µl reaction mixture consisted of 50 mM Tris —HCl, pH 7.9, 2 mM EDTA, 10% glycerol, 200 µM phenol, 1 µM hematin, 1–25 µl sample and 20 µM 1-[$^{14}$C] arachidonate (80.000–100.000 cpm/tube). After 45 seconds at room temperature, the reaction was terminated by adding 200 µl of 2N HCl and 750 µl water. An aliquot (950 µl) of the reaction mixture was loaded onto a 1 ml C_Sep-Pak (J. T. Baker, Phillipsburg, N.J.) which had been previously washed with 2–3 ml methanol and equilibrated with 5–6 ml distilled water. Oxygenated products were quantitatively eluted with 3 ml of acetonitrile, $H_2O$ and acetic acid (50:50:0.1, v/v) and the radioactivity in the eluate determined in a scintillation counter.

In this radiometric assay, Compound (16) was shown to be highly selective for COX II ($IC_{50}$=0.58–0.90 µM). By contrast, Compound (16) was essentially devoid of activity against COX I ($IC_{50}$>1000 µM, over three assays). Compound (16) displayed potent, time-dependent, reversible inhibition of COX II. At very low substrate concentration, Compound (16) displayed weak, competitive, non-time dependent inhibition of partially purified COX I.

With human foreskin fibroblasts incubated with Interleukin 1 and phorbol myristate acetate to induce expression of COX II, Compound (16) inhibited the production of $PGE_2$ elicited by calcium ionophore stimulation, with an $IC_{50}$= 0.12 µM. In washed human platelets stimulated with calcium ionophore to activate constitutive COX I, Compound (16) inhibited thromboxane $B_2$ production with an $IC_{50}$=2.3 µM. In human whole blood activated with ionophore (COX I) or lipopolysaccharide (COX II), Compound (16) inhibited $TxB_2$ production with $IC_{50}$=5.6 µM and 4.7 µM, respectively. The corresponding values for indomethacin in human whole blood are 0.13 µM and 1.7 µM.

A summary of activities of Compound (16) against COX I and COX II in cell-free enzyme preparations and whole cells is presented in Table 1. The following abbreviations are used: AA is arachidonic acid, IL-1 is interleukin 1, PMA is phorbol myristate acetate, A23187 is a calcium ionophore (Sigma), BSA is bovine serum albumin and LPS is a lipopolysaccharide (Sigma).

TABLE 1

| Enzyme Source | Assay Conditions | COX I IC$_{50}$, μM | COX II IC$_{50}$, μM |
|---|---|---|---|
| Human recombinant | 10 min incubation with Compound (16) | >1000 | 0.58 |
| -baculovirus | 45 sec incubation with 20 μM AA | >1000 | 0.90 |
| -partially purified | Separation of radioactive products | >1000 | 0.64 |
| Human foreskin fibroblasts | 30 min incubation with Compound (16) | | |
| -16 hr admulation with IL-1 and PMA | 10 min activation with | | |
| -washing, transfer to fresh media | a) 5 μM A23187 | | a) ≦0.1 |
| | b) 20 μM AA + FA-free BSA | | b) ≈2.7 |
| | EIA determination of PGE$_2$ | | |
| Human foreskin fibroblasts | 30 min incubation with Compound (16) | | 0.12 |
| -16 hr stimulation with IL-1 and PMA | 10 min activation, 5 μM A23187 | | 0.17 |
| -washing, transfer to fresh media | RIA determination of PGE$_2$ | | 0.14 |
| Human monocytes | 30 min incubation with Compound (16) | | |
| -freshly isolated | a) 10 min activation, A23187 + PMA | a) 5.20 | |
| -These cells may be expressing COX II | b) 30 min activation, A23187 + PMA | b) 0.31 | |
| constitutively | c) 10 min activation, 20 μM AA | c) 4.60 | |
| | d) 30 min activation, 20 μM AA | d) >10 | |
| | EIA determination of PGE$_2$ | | |
| Human adherent monocytes | 30 min incubation with Compound (16) | | |
| -18 hr stimulation with LPS | a) 10 min activation, A23187 + PMA | | a) 0.2 |
| -washing, transfer to fresh media | b) 30 min activation, A23187 + PMA | | b) <0.1 |
| | c) 10 min activation, 20 μM AA | | c) 2.8 |
| | d) 30 min activation, 20 μM AA | | d) 0.54 |
| | EIA determination of PGE$_2$ | | |
| Washed human platelets | 30 min incubation with Compound (16) | | |
| | a) 10 min activation, A23187 | a) 2.3 | |
| | b) 10 min activation, 20 μM AA | b) >100 | |
| | EIA determination of TxB$_2$ | | |
| Human whole blood | 30 min incubation with Compound (16) | 3.0 | |
| | 15 min activation, A23187 | | |
| | EIA determination of TxB$_2$ | | |
| Human whole blood | COX I- 15 min incubation with | | |
| -30 min assay for COX I | Compound (16); 30 min with A23187 | 5.6 | 4.56 |
| -5 hr assay for COX II | COX II- 5 hr incubation with | (3.8–7.3) | (4.36–4.80) |
| | Compound (16) and 10 μg/ml LPS | | |
| | RIA determination of TxB$_2$ | | |
| Rat whole blood | 15 min incubation with Compound (16) | 6 | |
| | 30 min activation with A23187 | 5 | |
| | EIA determination of TxB$_2$ | 4 | |

Numerous other compounds of the invention were evaluated under the radiometric assay conditions described above using human recombinant baculovirus expressed enzymes. As with Compound (16), these compounds also exhibited COX II selectivity, as can be seen below:

TABLE 2

| Compound # | COX I IC$_{50}$, μM | COX II IC$_{50}$, μM |
|---|---|---|
| 9 | >100 | 0.63 |
| 18 | 15 | 1.5 |
| 24 | 440 | 0.7 |
| 25 | 277 | 1.8 |
| 30 | 40 | 0.5 |
| 31 | 35 | 0.2 |
| 32 | 26.7 | 1.5 |
| 33 | 31.7 | 0.44 |
| 35 | 86 | 0.1 |
| 36 | 38 | 0.4 |
| 42 | 82 | 0.72 |
| 43 | 23 | 0.3 |
| 46 | >100 | 7.2 |
| 53 | 420 | 1 |
| 54 | 190 | 0.44 |
| 57 | 700 | 4.6 |
| 62 | 140 | 7 |
| 80 | ≧1000 | 0.7 |
| 81 | >300 | 0.44 |
| 82 | 20.6 | 0.81 |

TABLE 2-continued

| Compound # | COX I IC$_{50}$, μM | COX II IC$_{50}$, μM |
|---|---|---|
| 87 | >1000 | 0.9 |
| 88 | 100 | 0.55 |
| 89 | 8.1 | 2.3 |
| 95 | 140 | 1.3 |
| 100 | 300 | 1.5 |
| 102 | 260 | 3.1 |
| 107 | 21 | 2.3 |
| 114 | 82 | 0.66 |
| 116 | 0.92 | 0.18 |
| 118 | 76 | 0.8 |
| 120 | 8.9 | 0.8 |
| 121 | 6.3 | 0.23 |
| 122 | 0.074 | 0.063 |
| 123 | 3.5 | <0.03 |
| 124 | 94 | 0.54 |
| 125 | <10 | 1.6 |
| 126 | 61.4 | 0.97 |
| 127 | 57 | 0.67 |
| 129 | 3.4 | 0.067 |
| 130 | >100 | 0.58 |
| 131 | 5.3 | 0.12 |
| 133 | 3.7 | 0.07 |
| 135 | 52 | 0.35 |
| 136 | 829 | 3.06 |
| 140 | 48 | 0.53 |
| 141 | 4.9 | .125 |

TABLE 2-continued

| Compound # | COX I IC$_{50}$, μM | COX II IC$_{50}$, μM |
|---|---|---|
| 142 | 67 | 4.16 |
| 144 | 1 | 0.59 |
| 145 | 85 | 0.91 |
| 148 | 81.4 | 0.66 |
| 151 | 3.8 | <0.1 |
| 152 | 10 | 0.14 |
| 153 | >100 | 0.54 |
| 156 | 89 | 0.52 |
| 157 | 24.4 | 1.63 |
| 158 | 3.2 | 0.68 |
| 161 | 64.7 | 0.61 |
| 168 | 7.9 | 0.91 |

Example 33

Anti-inflammatory Activity

Carrageenan-induced paw edema in the rat has been used as the primary in vivo screen for anti-inflammatory activity of most NSAIDs. In this assay, NSAIDs typically produce a maximum inhibition of about 60%; therefore, the ED$_{30}$, which is the dose giving half-maximal inhibition, is the value reported.

Over a series of assays, in which Compound (16), suspended in SSV, was administered orally to rats 1 hour prior to injection of carrageenan, Compound (16) inhibited carrageenan-induced paw edema (ED$_{30}$=1.1±1.0 mg/kg).

Analysis of the data indicated that Compound (16) at the appropriate dose is capable of giving ~60% inhibition, the maximum amount achievable with NSAIDs.

Compound (16) was also tested in adjuvant-induced arthritis in the rat by dosing orally bid for 17 days beginning on the day of adjuvant injection. In a first test (0.1–5 mg/kg/day), Compound (16) gave 31% and 66% inhibitions at doses of .2 and 5 mg/kg/day, respectively. In a second test, 2, 5 and 10 mg/kg/day gave 43%, 48% and 52% inhibition, respectively, whereas indomethacin at 0.3 and 0.6 mg/kg/day gave 66% and 79% inhibition, respectively. In a third test at 1–100 mg/kg, Compound (16) produced dose dependent inhibition with a maximum of 80% inhibition at 100 mg/kg. Based on the data from thee three assays, Compound (16) has an ED$_{40}$=3.2±2.6 mg/kg.

Numerous other compounds of the invention were evaluated in a manner similar to Compound (16) and exhibited similar anti-inflammatory activity. These include Compounds (9), (18), (23)to (25), (29), (30), (32)to (35), (42), (43), (47), (53), (54), (80), (81), (95), (102), (112), (114), (116), (118), (120), (122) to (125), (127), (128), (140) to (142), (144), (145), (149), (152), (153), (161) and (169).

Example 34

Analgesic Activity

Analgetic activity is determined by the Phenylquinone-induced Mouse Writhing Assay, Hendershot, et al., *J. Pharmacol. Exp. Ther.*, 125:237–240 (1959). This assay is one of several acute assays which have been used to assess the analgesic activity of NSAIDs. At the appropriate time after test material administration, phenylquinone is injected intraperitoneally to mice, inducing a series of characteristic "writhing" responses, which are counted between 10 and 20 minutes after phenylquinone injection.

In this assay, Compound (16), suspended in SSV, was tested over the dose range of 1–100 mg/kg administered 20 or 60 minutes prior to phenylquinone challenge. Compound (16) gave 100% inhibition at 100 mg/kg and the ED$_{50}$≈10 mg/kg.

Compound (16) was also evaluated using an adjuvant-induced arthritis pain model in the rat, in which pain is assessed by eliciting a vocal response upon squeezing or flexing an inflamed ankle joint. A preliminary test of Compound (16) at 0.1, 1.0, 10 and 30 mg/kg showed that significant and prolonged analgesia is obtained at doses ≧10 mg/kg.

Numerous other compounds of the invention were evaluated in a manner similar to Compound (16) and exhibited similar analgesic activity. These include Compounds (18), (34), (35), (122) and (153).

Example 35

Gastrointestinal Erosive Activity

NSAIDs such as indomethacin are highly corrosive to the stomach and intestines of rats, and at relatively low doses administered sub-chronically (4–7 days), can cause erosions of the small intestine leading to frank ulceration, perforation and death due to peritonitis. For standard NSAIDs, the dose response is very steep with the lethal dose being only 4–5 fold that of the lowest dose producing minimal lesions, i.e., superficial mucosal damage.

When administered orally bid to rats for 4 days, Compound (16), suspended in SSV, caused no intestinal lesions at 25 mg/kg/day, and produced minimal lesions at 50 mg/kg/day (1 of 5 rats had a score of 1 on a scale of 0–5).

At 200 mg/kg/day, Compound (16) produced lesions in 4 of 5 rats, but the scores were no greater than 1. Lesions of this degree were detected by close observation of the entire length of the mucosal surface of ileum under appropriate reflected lighting conditions.

For a given ulcerogenic dose of drug, lesion intensity generally increases with duration of drug. Remarkable, no intestinal lesions were observed in the toxicology range-finding study in which rats were dosed with up to 300 mg/kg/day of Compound (16) for 14 days.

Numerous other compounds of the invention were evaluated in a manner similar to Compound (16) and exhibited similar GI erosive activity. These include Compounds (18), (95), (122) and (123).

Example 36

In Vivo Inhibition of Eicosanoid Synthesis

To examine the effect of Compound (16) on prostaglandin (PG) synthesis in inflamed tissues, Compound (16) was tested in a carrageenan-induced inflammation (air-pouch model) in rats. PGE$_2$ levels in the air-pouch exudate were measured by enzyme immunoassay in rats treated with 0.1–30 mg/kg of Compound (16). Relative to a vehicle treated control group, Compound (16) dose-dependently inhibited PGE$_2$ levels in the exudate with an IC$_{50}$≈0.7–2 mg/kg. The NSAID indomethacin at 2–5 mg/kg also inhibited PGE$_2$ in the exudates to >70%.

To test the effects of Compound (16) on PG synthesis in non-inflamed tissue, PGE$_2$ levels were measured in the stomach of rats from the above experiments. Compound (16) at any of the concentrations tested (0.1–30 mg/kg had no significant inhibition of stomach $PGE_2$, while indomethacin at 2–5 mg/kg caused >80% inhibition of stomach $PGE_2$.

Numerous other compounds of the invention were evaluated in the above manner for the inhibition of PG synthesis in inflamed and non-inflamed tissues and exhibited similar activity. These include Compound (9), (35), (122), (123), (129), (145), (149), (153) and (161).

Example 37

Pharmacokinetics

The pharmacokinetics of Compound (16) was studied in rat and monkey after intravenous and oral administration in solution (ethanol/polyethylene glycol/water, 1/5/4) or SSV.

Compound (16) was shown to have good bioavailability in rats and monkeys (40–80%). The compound also exhibited dose proportionality over a broad range of doses (1–300 mg/kg) and has a half-life of 2–3 hours after intravenous dosing.

Example 38

Subchronic Toxicity

A two week range finding study in rats was carried out at daily doses of 10, 30, 100 and 300 mg/kg of Compound (16). All animals survived the study and no adverse clinical signs were noted. No clinical chemistry abnormalities were detected and there were no drug-related gross necropsy findings. In particular, no lesions were noted in the stomach or intestines. There were no histopathological findings.

A two week range finding study in cynomolgus monkeys was carried out at daily doses of 10, 30, 100 and 300 mg/kg of Compound (16). No abnormalities were observed in clinical signs, clinical chemistry, gross pathology or histopathology.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A compound having the structure:

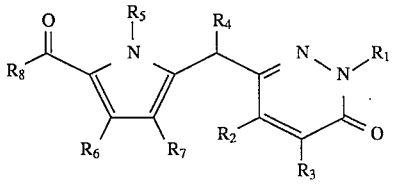

wherein:

$R_1$ is —H, lower alkyl, halo-lower alkyl, acetyl (optionally substituted with one to three groups selected from lower alkyl, acetoxy, and amino), —$(CHR_{24})(CH_2)_nR_{14}$, —$(CHR_{24})(CH_2)_nC(O)R_{15}$, —$(CHR_{24})(CH_2)_nC(O)NR_{16}R_{17}$ or $CHR_{24}R_{18}$; where n is an integer from 0–5, $R_{14}$ is —CN, —OH, lower alkoxy, lower acyloxy (optionally substituted with One to three groups selected from lower alkyl, acetoxy, and amino), lower dialkylamino, lower alkylthio, lower alkylsulfinyl, lower alkylsulfonyl, lower alkene, lower alkyne or methane sulfonamido; $R_{15}$ is lower alkoxy; $R_{16}$ and $R_{17}$ are independently selected from the group consisting of —H and lower alkyl; $R_{18}$ is:

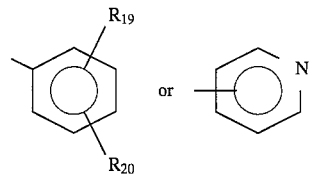

where $R_{19}$ and $R_{20}$ are independently selected from the group consisting of —CN, halo, lower alkoxy and lower alkyl; and $R_{24}$ is —H, lower alkyl or phenyl;

$R_2$ and $R_3$ are independently selected from the group consisting of —H, halo and —$CH_3$;

$R_4$ is —H, lower alkyl or —CN;

$R_5$ is —H or lower alkyl;

$R_6$ and $R_7$ are independently selected from the group consisting of —H, halo, lower alkyl, lower alkoxy and lower alkylthio; and $R_8$ is:

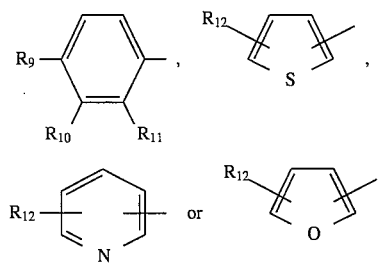

where $R_9$ is —H, halo, lower alkyl, halo-lower alkyl, amino, lower dialkylamino, lower alkyl amido, lower alkylthio, lower alkoxy, lower alkene and lower alkyne; $R_{10}$ and $R_{11}$ are —H; and $R_{12}$ is —H, Cl or —$CH_3$;

or a pharmaceutically acceptable salt thereof.

2. A compound of claim 1 wherein $R_1$ is —H, —$(CHR_{24})(CH_2)_nR_{14}$ or —$CHR_{24}R_{18}$.

3. A compound of claim 2 wherein $R_1$ is —H, —$CH_2CN$ or —$CHR_{24}R_{18}$, where $R_{18}$ is a benzene ring and $R_{19}$ and $R_{20}$ are independently selected from the group consisting of —CN, halo and lower alkyl.

4. A compound of claim 3 wherein $R_1$ is —H.

5. A compound of claim 3 wherein $R_{19}$ and $R_{20}$ are independently selected from the group consisting of —CN, —Cl or —$CH_3$.

6. A compound of claim 1 wherein $R_2$ is —H.

7. A compound of claim 1 wherein $R_3$ is —H.

8. A compound of claim 1 wherein $R_4$ is —H.

9. A compound of claim 1 wherein $R_5$ is lower alkyl.

10. A compound of claim 9 wherein $R_5$ is —$CH_3$.

11. A compound of claim 1 wherein $R_6$ is lower alkyl.

12. A compound of claim 11 wherein $R_6$ is —$CH_3$.

13. A compound of claim 1 wherein $R_7$ is —H, halo or lower alkyl.

14. A compound of claim 13 wherein $R_7$ is —H, —Cl or —$CH_3$.

15. A compound of claim 14 wherein $R_7$ is —H.

16. A compound of claim 1 wherein $R_8$ is a benzene ring.

17. A compound of claim 16 wherein $R_9$ is halo, lower alkyl, lower alkoxy, lower alkylthio, or lower alkene.

18. A compound of claim 17 wherein $R_9$ is —Cl, —Br, —SCH$_3$, or —CHCH$_2$.

19. A compound of claim 18 wherein $R_9$ is —Cl.

20. A compound of claim 1 wherein $R_1$, $R_2$, $R_3$ and $R_4$ are —H, $R_5$ and $R_6$ are —CH$_3$; $R_7$ is —H; $R_8$ is a benzene ring; and $R_9$ is —H, —Cl, —Br, —CH$_3$, —OCH$_3$, —CHCH$_2$, —SCH$_3$, or —CH$_2$CH$_3$.

21. A compound of claim 20 wherein $R_9$ is —Cl.

22. A compound of claim 20 wherein $R_9$ is —Br.

23. A compound of claim 1 wherein $R_1$, $R_2$, $R_3$ and $R_4$ are —H, $R_5$ is —CH$_3$; $R_6$ is —H; $R_7$ is —H; $R_8$ is a benzene ring; and $R_9$ is —H, —Br, —Cl, —F, —CH$_3$, —C(CH$_3$)$_3$, —CH(CH$_3$)$_2$, cyclopropyl, —CF$_3$, —N(CH$_3$)$_2$, —SCH$_3$, SCH$_2$ CH$_3$, —CH$_2$CH$_3$, —CHCH$_2$, —C≡CH, —NHCOCH$_3$, —OCH$_3$, —O(CH$_2$)$_2$CH$_3$, —OCH(CH$_3$)$_2$, or —OCH$_2$CH$_3$.

24. A compound of claim 1 wherein $R_1$, $R_2$, $R_3$ and $R_4$ are —H, $R_5$ and $R_6$ are —CH$_3$; $R_7$ is —H; $R_8$ is a benzene ring; and $R_9$ is —F.

25. A compound of claim 1 wherein $R_1$, $R_2$, $R_3$ and $R_4$ are —H, $R_5$ is —CH$_3$; $R_6$ is —SCH$_3$; $R_7$ is —H; $R_8$ is a benzene ring; and $R_9$ is —Cl.

26. A compound of claim 1 wherein $R_1$, $R_2$, $R_3$ and $R_4$ are —H, $R_5$ is —CH$_3$; $R_6$ is —Cl; $R_7$ is —H; $R_8$ is a benzene ring; and $R_9$ is —CH$_3$, —Cl, or —OCH$_3$.

27. A compound of claim 1 wherein $R_1$, $R_2$ and $R_3$ are —H; $R_4$ is —CN or —CH$_3$; $R_5$ and $R_6$ are —CH$_3$; $R_7$ is —H; $R_8$ is a benzene ring; and $R_9$ is —Cl.

28. A compound of claim 1 wherein $R_1$, $R_2$ and $R_3$ are —H; $R_4$ is —H; $R_5$ is —CH$_2$CH$_3$; $R_6$ is —H; $R_7$ is —H; $R_8$ is a benzene ring; and $R_9$ is —CH$_3$.

29. A compound of claim 1 wherein $R_1$, $R_2$ and $R_3$ are —H; $R_4$ is —CH$_3$; $R_5$ is —CH$_3$; $R_6$ is —H; $R_7$ is —H; $R_8$ is a benzene ring; and $R_9$ is —CH$_3$.

30. A compound of claim 1 wherein $R_1$, $R_2$, $R_3$ and $R_4$ are —H; $R_5$ and $R_6$ are —CH$_3$; $R_7$ is —Cl or —Br; $R_8$ is a benzene ring; and $R_9$ is —Cl.

31. A compound of claim 1 wherein $R_1$, $R_2$, $R_3$ and $R_4$ are —H; $R_5$ is —CH$_3$; $R_6$ is —H; $R_7$ is —Cl; $R_8$ is a benzene ring; and $R_9$ is —CH$_3$ or —OCH$_3$.

32. A compound of claim 1 wherein $R_1$, $R_2$, $R_3$ and $R_4$ are —H; $R_5$ is —CH$_3$; $R_6$ is —CH$_3$; $R_7$ is —Cl; $R_8$ is a benzene ring; and $R_9$ is —H.

33. A compound of claim 1 wherein $R_1$, $R_2$, $R_3$ and $R_4$ are —H; $R_5$ is —CH$_3$; $R_6$ is —SCH$_3$; $R_8$ is —H; $R_8$ is a benzene ring; and $R_9$ is —CH$_3$.

34. A compound of claim 1 wherein $R_1$, $R_2$, $R_3$ and $R_4$ are —H; $R_5$ is —CH$_3$; $R_6$ is —H; $R_7$ is —Br; $R_8$ is a benzene ring; and $R_9$ is —CH$_2$.

35. A compound of claim 1 wherein $R_1$ is —H; $R_2$ is —H or —CH$_3$; $R_3$ is —CH$_3$; $R_4$ is —H, $R_5$ and $R_6$ are —CH$_3$; $R_7$ is —H; $R_8$ is a benzene ring; and $R_9$ is —Cl.

36. A compound of claim 1 wherein $R_1$, $R_2$, $R_3$ and $R_4$ are —H; $R_5$ is —CH$_3$; $R_6$ is —H; $R_7$ is —H; $R_8$ is 2-thienyl, 4-pyridyl, 3-pyridyl, 2-furyl or 3-furyl; and $R_{12}$ is —H.

37. A compound of claim 1 wherein $R_1$, $R_2$, $R_3$ and $R_4$ are —H; $R_5$ is —CH$_3$; $R_6$ is —H; $R_7$ is —H; $R_8$ is 2-thiophene; and $R_{12}$ is —CH$_3$.

38. A compound of claim 1 wherein $R_1$, $R_2$, $R_3$ and $R_4$ are —H; $R_5$ is —CH$_3$; $R_6$ is —CH$_3$; $R_7$ is —H; $R_8$ is 2-thiophene; and $R_{12}$ is —H.

39. A compound of claim 1 wherein $R_1$ is —CH$_3$,—C(O)CH$_3$, —(CH$_2$)$_2$F, —(CH$_2$)CCH, —(CH$_2$)CHCH$_2$, —(CH$_2$) Cl or —C(O)C(CH$_3$)$_2$OC(O)CH$_3$; $R_2$, $R_3$ and $R_5$ are —H; $R_5$ and $R_6$ are —CH$_3$; $R_7$ is —H; and $R_8$ is a benzene ring, where $R_9$ is —Cl.

40. A compound of claim 1 wherein $R_1$ is —(CH$_2$)$_2$OH, —CH$_2$CN, —(CH$_2$)$_2$OCH$_3$, —(CH$_2$)$_2$OC(O)CH$_3$, —(CH$_2$)$_2$NHS(O)$_2$CH$_3$, —(CH$_2$)$_3$OH, —(CH$_2$)$_2$CN, —CH$_2$OC(O)C(CH$_3$)$_3$, —CH$_2$OH, —CH$_2$OC(O)CH$_3$, —(CH$_2$)C(O)OCH$_3$, —CH$_2$C(O)N(CH$_3$)$_2$, —CH$_2$C(O)NH$_2$, —CH$_2$C(O)NH(CH$_3$), —CH$_2$C(O)NH(CH$_2$)$_3$(CH$_3$), —CH$_2$C(O)N(CH$_2$CH$_3$)$_2$ or —CH$_2$C (O)NHCH(CH$_3$)CH$_2$CH$_3$; $R_2$, $R_3$ and $R_4$ are —H; $R_5$ and $R_6$ are —CH$_3$; $R_7$ is —H; and $R_8$ is a benzene ring, where $R_9$ is —Cl.

41. A compound of claim 40 wherein $R_1$ wherein $R_1$ is —CH$_2$CN.

42. A compound of claim 40 wherein $R_1$ is —CH$_2$OH.

43. A compound of claim 1 wherein $R_1$ is 3,4-dichlorobenzyl, benzyl, 4-fluorobenzyl, 4-chlorobenzyl, 4-methylbenzyl, 2-fluorobenzyl, 4-cyanobenzyl, 3-fluorobenzyl, 3-cyanobenzyl, 2-cyanobenzyl, 2,6-dimethylbenzyl, 2,6-dichlorobenzyl, 2-pyridyl or 4-methoxybenzyl; $R_2$, $R_3$ and $R_4$ are —H; $R_5$ and $R_6$ are —CH$_3$; $R_7$ is —H; and $R_5$ is a benzene ring, where $R_9$ is —Cl.

44. A compound having the structure:

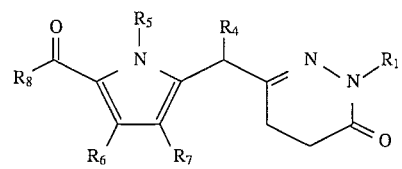

wherein $R_1$ is —H, lower alkyl, halo-lower alkyl, acetyl (optionally substituted with one to three groups selected from lower alkyl, acetoxy, and amino), —(CHR$_{24}$)(CH$_2$)$_n$R$_{14}$, —(CHR$_{24}$)(CH$_2$)$_n$C(O)R$_{15}$, —(CHR$_{24}$)(CH$_2$)$_n$C(O)NR$_{16}$R$_{17}$ or —(CHR$_{24}$R$_{18}$; where n is an integer from 0–5, $R_{14}$ is —CN, —OH, lower alkoxy, lower acyloxy (optionally substituted with one to three groups selected from lower alkyl, acetoxy, and amino), lower dialkylamino, lower alkylthio, lower alkylsulfinyl, lower alkylsulfonyl, lower alkene, lower alkyne or methane sulfonamido; $R_{15}$ is lower alkoxy; $R_{16}$ and $R_{17}$ are independently selected from the group consisting of —H and lower alkyl; $R_{18}$ is:

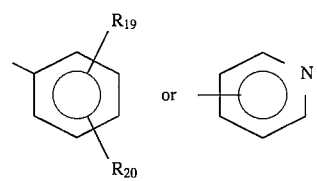

were $R_{19}$ and $R_{20}$ are independently selected from the group consisting of —CN, halo, lower alkoxy and lower alkyl; and $R_{24}$ is —H, lower alkyl or phenyl;

$R_4$ is —H, lower alkyl or —CN;

$R_5$ is —H or lower alkyl;

$R_6$ and $R_7$ are independently selected from the group consisting of —H, halo, lower alkyl, lower alkoxy and lower alkylthio; and $R_8$ is:

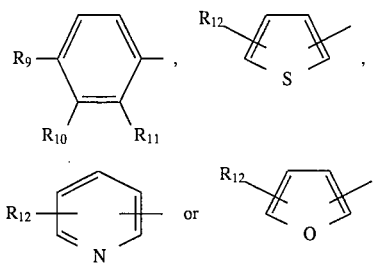

where $R_9$ is —H, halo, lower alkyl, halo-lower alkyl, amino, lower dialkylamino, lower alkyl amido, lower alkylthio, lower alkoxy, lower alkene and lower alkyne; $R_{10}$ and $R_{11}$ are —H; and $R_{12}$ is —H, —Cl or —CH$_3$; or a pharmaceutically acceptable salt thereof.

45. A compound of claim 44 wherein $R_1$ is —H, —(CHR$_{24}$) (CH$_2$)$_n$R$_{14}$ or —CHR$_{24}$R$_{18}$.

46. A compound of claim 45 wherein $R_1$ is —H, —CH$_2$CN or —CHR$_{24}$R$_{18}$, where R$_{18}$ is a benzene ring and R$_{19}$ and R$_{20}$ are independently selected from the group consisting of —CN, halo and lower alkyl.

47. A compound of claim 46 wherein $R_1$ is —H.

48. A compound of claim 46 wherein R$_{19}$ and R$_{20}$ are independently selected from the group consisting of —CN, —Cl or —CH$_3$.

49. A compound of claim 44 wherein $R_4$ is —H.

50. A compound of claim 44 wherein $R_5$ is lower alkyl.

51. A compound of claim 50 wherein $R_5$ is —CH$_3$.

52. A compound of claim 44 wherein $R_6$ is lower alkyl.

53. A compound of claim 52 wherein $R_6$ is —CH$_3$.

54. A compound of claim 44 wherein $R_7$ is —H, halo or lower alkyl.

55. A compound of claim 54 wherein $R_7$ is —H, —Cl or —CH$_3$.

56. A compound of claim 55 wherein $R_7$ is —H.

57. A compound of claim 44 wherein $R_8$ is a benzene ring.

58. A compound of claim 57 wherein $R_9$ is halo, lower alkyl, lower alkoxy, lower alkylthio, or lower alkene.

59. A compound of claim 58 wherein $R_9$ is —Cl, —Br, —SCH$_3$, or —CHCH$_2$.

60. A compound of claim 59 wherein $R_9$ is —Cl.

61. A compound of claim 44, wherein $R_1$ is —H; $R_4$ is —H; $R_5$ is —CH$_3$; $R_6$ is —CH$_3$; $R_7$ is —H; and $R_8$ is a benzene ring, where $R_9$ is —Cl.

62. A compound of claim 44 wherein $R_1$ is —H; $R_4$ is —H; $R_5$ is —CH$_3$; $R_6$ is —H; $R_7$ is —H; and $R_8$ is a benzene ring, where $R_9$ is —CH$_3$.

63. A compound having the structure:

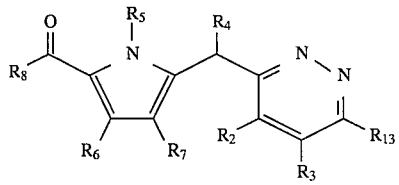

wherein:

$R_2$ and $R_3$ are independently selected from the group consisting of —H, halo and —CH$_3$;

$R_4$ is —H, lower alkyl or —CN;

$R_5$ is —H or lower alkyl;

$R_6$ and $R_7$ are independently selected from the group consisting of —H, halo, lower alkyl, lower alkoxy and lower alkylthio;

$R_8$ is:

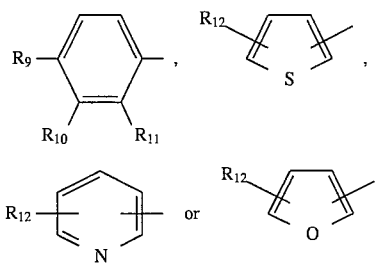

where $R_9$ is —H, halo, lower alkyl, halo-lower alkyl, amino, lower dialkylamino, lower alkyl amido, lower alkylthio, lower alkoxy, lower alkene and lower alkyne; $R_{10}$ and $R_{11}$ are —H; and $R_{12}$ is —H, —Cl or —CH$_3$; and $R_{13}$ is lower alkoxy, mercapto, lower alkylthio, —NR$_{21}$R$_{22}$ or —O—(CH$_2$)$_m$—NR$_{21}$R$_{22}$; where m is an integer from 1 to 6, R$_{21}$ is —H or lower alkyl and R$_{22}$ is —H or lower alkyl, or —NR$_{21}$R$_{22}$ is morpholino;

or a pharmaceutically acceptable salt thereof.

64. A compound of claim 63 wherein $R_2$ is —H.

65. A compound of claim 63 wherein $R_3$ is —H.

66. A compound of claim 63 wherein $R_4$ is —H.

67. A compound of claim 63 wherein $R_5$ is lower alkyl.

68. A compound of claim 67 wherein $R_5$ is —CH$_3$.

69. A compound of claim 63 wherein $R_6$ is lower alkyl.

70. A compound of claim 69 wherein $R_6$ is —CH$_{13}$.

71. A compound of claim 63 wherein $R_7$ is —H, halo or lower alkyl.

72. A compound of claim 71 wherein $R_7$ is —H, —Cl or —CH$_3$.

73. A compound of claim 72 wherein $R_7$ is —H.

74. A compound of claim 63 wherein $R_8$ is a benzene ring.

75. A compound of claim 74 wherein $R_9$ is halo, lower alkyl, lower alkoxy, lower alkylthio, or lower alkene.

76. A compound of claim 75 wherein $R_9$ is —Cl, —Br, —SCH$_3$, or —CHCH$_2$.

77. A compound of claim 76 wherein $R_9$ wherein $R_9$ is —Cl.

78. A compound of claim 63 wherein R$_{13}$ is lower alkoxy.

79. A compound of claim 63 wherein $R_2$, $R_3$ and $R_4$ are —H; $R_5$ and $R_6$ are—CH$_3$; $R_7$ is —H; $R_8$ is a benzene ring, where $R_9$ is —Cl; and R$_{13}$ is —OCH$_3$, —OCH(CH$_3$)$_2$, —OCH$_2$CH$_3$, —O(CH$_2$)$_2$-morpholino (HCl salt), —NH$_2$ or —SH.

80. A compound having the structure:

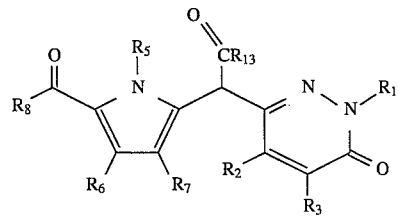

wherein:

$R_1$ is —H, lower alkyl, halo-lower alkyl, acetyl (optionally substituted with one to three groups selected from lower alkyl, acetoxy, and ammo, —(CHR$_{24}$)(CH$_2$)$_n$R$_{14}$, —(CHR$_{24}$) (CH$_2$)$_n$C(O)R$_{15}$, —(CHR$_{24}$) (CH$_2$)$_n$C(O)NR$_{16}$R$_{17}$ or —CHR$_{24}$R$_{18}$; where n is an integer from 0–5, R$_{14}$ is —CN, —OH, lower alkoxy, lower acyloxy (optionally substituted with one to three groups selected from lower alkyl, acetoxy, and amino), lower dialkylamino, lower alkylthio, lower alkylsulfinyl, lower alkylsulfonyl, lower alkene, lower alkyne or methane sulfonamido; $R_{15}$ is lower alkoxy; $R_{16}$ and $R_{17}$ are independently selected from the group consisting of —H and lower alkyl; $R_{18}$ is:

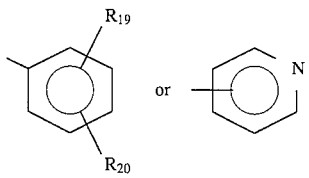

where $R_{19}$ and $R_{20}$ are independently selected from the group consisting of —CN, halo, lower alkoxy and lower alkyl; and $R_{24}$ is —H, lower alkyl or phenyl;

$R_2$ and $R_3$ are independently selected from the group consisting of —H, halo and —$CH_3$;

$R_5$ is —H or lower alkyl;

$R_6$ and $R_7$ are independently selected from the group consisting of —H, halo, lower alkyl, lower alkoxy and lower alkylthio;

$R_8$ is:

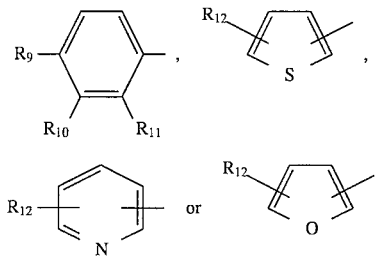

where $R_9$ is —H, halo, lower alkyl, halo-lower alkyl, amino, lower dialkylamino, lower alkyl amido, lower alkylthio, lower alkoxy, lower alkene and lower alkyne; $R_{10}$ and $R_{11}$ are —H; and $R_{12}$ is —H, —Cl or —$CH_3$; and $R_{13}$ is lower alkoxy, mercapto, lower alkylthio, —$NR_{21}R_{22}$ or —O—$(CH_2)_m$—$NR_{21}R_{22}$; where m is an integer from 1 to 6, $R_{21}$ is —H or lower alkyl and $R_{22}$ is —H or lower alkyl, or —$NR_{21}R_{22}$ is morpholino;

or a pharmaceutically acceptable salt thereof.

81. A compound of claim 80 wherein $R_1$ is —H, —$(CHR_{24})(CH_2)_nR_{14}$ or —$CHR_{24}R_{18}$.

82. A compound of claim 81 wherein $R_1$ is —H, —$CH_2CN$ or —$CHR_{24}R_{18}$, where $R_{18}$ is a benzene ring and $R_{19}$ and $R_{20}$ are independently selected from the group consisting of —CN, halo and lower alkyl.

83. A compound of claim 82 wherein $R_1$ is —H.

84. A compound of claim 82 wherein $R_{19}$ and $R_{20}$ are independently selected from the group consisting of —CN, —Cl or —$CH_3$.

85. A compound of claim 80 wherein $R_2$ is —H.

86. A compound of claim 80 wherein $R_3$ is —H.

87. A compound of claim 80 wherein $R_5$ is lower alkyl.

88. A compound of claim 87 wherein $R_5$ is —$CH_3$.

89. A compound of claim 80 wherein $R_6$ is lower alkyl.

90. A compound of claim 89 wherein $R_6$ is —$CH_3$.

91. A compound of claim 80 wherein $R_7$ is —H, halo or lower alkyl.

92. A compound of claim 92 wherein $R_7$ wherein $R_7$ is —H, —Cl or —$CH_3$.

93. A compound of claim 92 wherein $R_7$ is —H.

94. A compound of claim 80 wherein $R_8$ is a benzene ring.

95. A compound of claim 5 wherein $R_9$ is halo, lower alkyl, lower alkoxy, lower alkylthio, or lower alkene.

96. A compound of claim 95 wherein $R_9$ is —Cl, —Br, —$SCH_3$, or —$CHCH_3$.

97. A compound of claim 96 wherein $R_9$ is —Cl.

98. A compound of claim 80 wherein $R_{13}$ is lower alkoxy.

99. A compound of claim 80 wherein $R_1$, $R_2$ and $R_3$ are —H; $R_5$ and $R_6$ are —$CH_3$; $R_7$ is —H; $R_8$ is a benzene ring, where $R_9$ is —Cl; and where $R_{13}$ is —$O(CH_2)_2$-morpholino (HCl salt) or —$OCH_3$.

100. A pharmaceutical composition comprising (a) a therapeutically effective amount of a compound of claim 1 or a pharmaceutically acceptable salt thereof and (b) at least one pharmaceutically acceptable excipient.

101. A pharmaceutical composition of claim 100, wherein $R_1$ is —H, —$(CHR_{24})(CH_2)_nR_{14}$ or —$CHR_{24}R_{18}$; $R_2$, $R_3$ and $R_4$ are —H; $R_5$ and $R_6$ are lower alkyl; $R_7$ is —H, halo or lower alkyl; and $R_8$ is a benzene ring, where $R_9$ is halo, lower alkyl, lower alkoxy, lower alkylthio, or lower alkene.

102. A pharmaceutical composition comprising (a) a therapeutically effective amount of a compound of claim 44 or a pharmaceutically acceptable salt thereof and (b) at least one pharmaceutically acceptable excipient.

103. A pharmaceutical composition of claim 102, wherein $R_1$ is —H, —$(CHR_{24})(CH_2)_nR_{14}$ or —$CHR_{24}$ $R_{18}$; $R_4$ is —H; $R_5$ and $R_6$ are lower alkyl; $R_7$ is —H, halo or lower alkyl; and $R_8$ is a benzene ring, where $R_9$ is halo, lower alkyl, lower alkoxy, lower alkylthio, or lower alkene.

104. A pharmaceutical composition comprising (a) a therapeutically effective amount of a compound of claim 63 or a pharmaceutically acceptable salt thereof and (b) at least one pharmaceutically acceptable excipient.

105. A pharmaceutical composition of claim 104, wherein $R_2$, $R_3$ and $R_4$ are —H; $R_5$ and $R_6$ are lower alkyl; $R_7$ is —H, halo or lower alkyl; $R_8$ is a benzene ring, where $R_9$ is halo, lower alkyl, lower alkoxy, lower alkylthio, or lower alkene; and $R_{13}$ is lower alkoxy.

106. A pharmaceutical composition comprising (a) a therapeutically effective amount of a compound of claim 80 or a pharmaceutically acceptable salt thereof and (b) at least one pharmaceutically acceptable excipient.

107. A pharmaceutical composition of claim 119; wherein $R_1$ is —H, —$(CHR_{24})(CH_2)_nR_{14}$ or —$CHR_{24}R_{18}$; $R_2$ and $R_3$ are —H; $R_5$ and $R_6$ are lower alkyl; $R_7$ is —H, halo or lower alkyl; $R_8$ is a benzene ring, where $R_9$ is halo, lower alkyl, lower alkoxy, lower alkylthio, or lower alkene lower alkoxy.

108. A method of treating inflammation and pain comprising the step of administering to a mammal in need of said treatment a therapeutically effective amount of a compound of claim 1 or a pharmaceutically acceptable salt thereof.

109. A method of claim 108, wherein $R_1$ is —H, —$(CHR_{24})(CH_2)_nR_{14}$ or —$CHR_{24}R_{18}$; $R_2$, $R_3$ and $R_4$ are —H; $R_5$ and $R_6$ are lower alkyl; $R_7$ is —H, halo or lower alkyl; and $R_8$ is a benzene ring, where $R_9$ is halo, lower alkyl, lower alkoxy, lower alkylthio, or lower alkene.

110. A method of treating inflammation and pain comprising the step of administering to a mammal in need of said treatment a therapeutically effective amount of a compound of claim 44 or a pharmaceutically acceptable salt thereof.

111. A method of claim 110, wherein $R_1$ is —H, —$(CHR_{24})(CH_2)_nR_{14}$ or —$CHR_{24}R_{18}$; $R_4$ is —H; $R_5$ and $R_6$ are lower alkyl; $R_7$ is —H, halo or lower alkyl; and $R_8$ is a benzene ring, where $R_9$ is halo, lower alkyl, lower alkoxy, lower alkylthio, or lower alkene.

112. A method of treating inflammation and pain comprising the step of administering to a mammal in need of said treatment a therapeutically effective amount of a compound of claim 63 or a pharmaceutically acceptable salt thereof.

113. A method of claim 112, wherein $R_2$, $R_3$ and $R_4$ are —H; $R_5$ and $R_6$ are lower alkyl; $R_7$ is —H, halo or lower alkyl; $R_8$ is a benzene ring, where $R_1$ is halo, lower alkyl, lower alkoxy, lower alkylthio, or lower alkene; and $R_{13}$ is lower alkoxy.

114. A method of treating inflammation and pain comprising the step of administering to a mammal in need of said treatment a therapeutically effective amount of a compound of claim 80 or a pharmaceutically acceptable salt thereof.

115. A method of claim 114, wherein $R_1$ is —H, —(CHR$_{24}$)(CH$_2$)$_n$R$_{14}$ or —CHR$_{24}$R$_{18}$; $R_2$ and $R_3$ are —H; $R_5$ and $R_6$ are lower alkyl; $R_7$ is —H, halo or lower alkyl; $R_8$ is a benzene ring, where $R_9$ is halo, lower alkyl, lower alkoxy, lower alkylthio, or lower alkene; and $R_{13}$ is lower alkoxy.

* * * * *

UNITED STATES PATENT AND TRADEMARK OFFICE
CERTIFICATE OF CORRECTION

PATENT NO. : 5,622,948
DATED : Apr. 22, 1997
INVENTOR(S) : Dunn et al.

It is certified that error appears in the above-indentified patent and that said Letters Patent is hereby corrected as shown below:

Claim 33, at column 55, line 44 "$R_8$ is –H" should read -- $R_7$ is –H --.

Claim 34, at column 55, line 48 "$R_9$ is –$CH_2$" should read -- $R_9$ is –$CH_3$ --.

Claim 35, at column 55, line 50 "$R_5$ *and $R_6$* are –$CH_3$" should read -- $R_5$ and $R_6$ are –$CH_3$ --.

Claim 39, at column 55, line 63 "$R_2$, $R_3$ and $R_5$" should read -- $R_2$, $R_3$ and $R_4$ --.

Claim 41, column 56, line 10 delete the second occurrence of "wherein $R_1$".

Claim 43, column 56, line 21 "$R_5$ is a benzene ring" should read -- $R_8$ is a benzene ring --.

Claim 70, column 58, line 31 "$R_6$ is –$CH_{13}$." should read -- $R_6$ is –$CH_3$. --.

Claim 77, column 58, line 42 delete the second occurrence of "wherein $R_9$".

Claim 80, column 58, line 64 "ammo" should read -- amino) --.

Claim 92, column 60, line 1 delete the second occurrence of "wherein $R_7$".

Claim 95, column 60, line 5 "claim 5" should read -- claim 94 --.

Claim 96, column 60, line 8 "–$CHCH_3$." should read -- –$CHCH_2$. --.

UNITED STATES PATENT AND TRADEMARK OFFICE
CERTIFICATE OF CORRECTION

PATENT NO. : 5,622,948
DATED : Apr. 22, 1997
INVENTOR(S) : Dunn et al.

It is certified that error appears in the above-indentified patent and that said Letters Patent is hereby corrected as shown below:

Claim 107, column 60, line 46 "claim 119" should read -- claim 106 --.

Claim 107, column 60, line 50 insert -- , and $R_{13}$ is -- after "alkene".

Claim 113, column 61, line 9 "$R_1$" should read -- $R_9$ --.

Signed and Sealed this

Ninth Day of September, 1997

BRUCE LEHMAN

Attest:

Attesting Officer

Commissioner of Patents and Trademarks